(12) United States Patent
Muhanna

(10) Patent No.: US 8,641,765 B2
(45) Date of Patent: Feb. 4, 2014

(54) POSTERIOR SPINAL IMPLANT SYSTEM

(76) Inventor: Nabil L. Muhanna, Gainesville, GA (US)

( * ) Notice: Subject to any disclaimer, the term of this patent is extended or adjusted under 35 U.S.C. 154(b) by 459 days.

(21) Appl. No.: 12/820,754

(22) Filed: Jun. 22, 2010

(65) Prior Publication Data

US 2011/0040382 A1 Feb. 17, 2011

Related U.S. Application Data

(60) Provisional application No. 61/233,246, filed on Aug. 12, 2009, provisional application No. 61/315,531, filed on Mar. 19, 2010.

(51) Int. Cl.
*A61F 2/44* (2006.01)
(52) U.S. Cl.
USPC ............................. 623/17.16; 623/17.11
(58) Field of Classification Search
USPC ................. 623/17.11–17.16; 606/246–249
See application file for complete search history.

(56) References Cited

U.S. PATENT DOCUMENTS

| | | | |
|---|---|---|---|
| 4,904,261 A | 2/1990 | Dove et al. | |
| 5,397,364 A | 3/1995 | Kozak et al. | |
| 5,425,772 A * | 6/1995 | Brantigan | 623/17.11 |
| 5,556,431 A | 9/1996 | Büttner-Janz | |
| 6,066,175 A | 5/2000 | Henderson et al. | |
| 6,235,059 B1 | 5/2001 | Benezech et al. | |
| 6,342,074 B1 | 1/2002 | Simpson | |
| 6,423,063 B1 | 7/2002 | Bonutti | |
| 6,491,724 B1 * | 12/2002 | Ferree | 623/17.11 |
| 6,984,234 B2 | 1/2006 | Bray | |
| 7,172,627 B2 * | 2/2007 | Fiere et al. | 623/17.11 |
| 7,232,464 B2 | 6/2007 | Mathieu et al. | |
| 7,618,456 B2 | 11/2009 | Mathieu et al. | |
| 2002/0082597 A1 * | 6/2002 | Fraser | 606/61 |
| 2006/0030851 A1 * | 2/2006 | Bray et al. | 606/69 |
| 2010/0057206 A1 * | 3/2010 | Duffield et al. | 623/17.16 |

* cited by examiner

*Primary Examiner* — Nicholas Woodall
(74) *Attorney, Agent, or Firm* — Womble Carlyle Sandridge & Rice LLP

(57) ABSTRACT

Disclosed is a spinal implant comprising an implant spacer body and a plate. The spinal implant may be installed into an inter-vertebral space between adjacent vertebrae and may be installed from a patient's posterior. The implant spacer body tapers from the anterior toward the posterior and may be tapered at the anterior end to facilitate installation. Some embodiments disclosed herein may comprise an implant spacer body only, some embodiments may comprise a plate only, and some embodiments may comprise an implant spacer body and a plate.

17 Claims, 13 Drawing Sheets

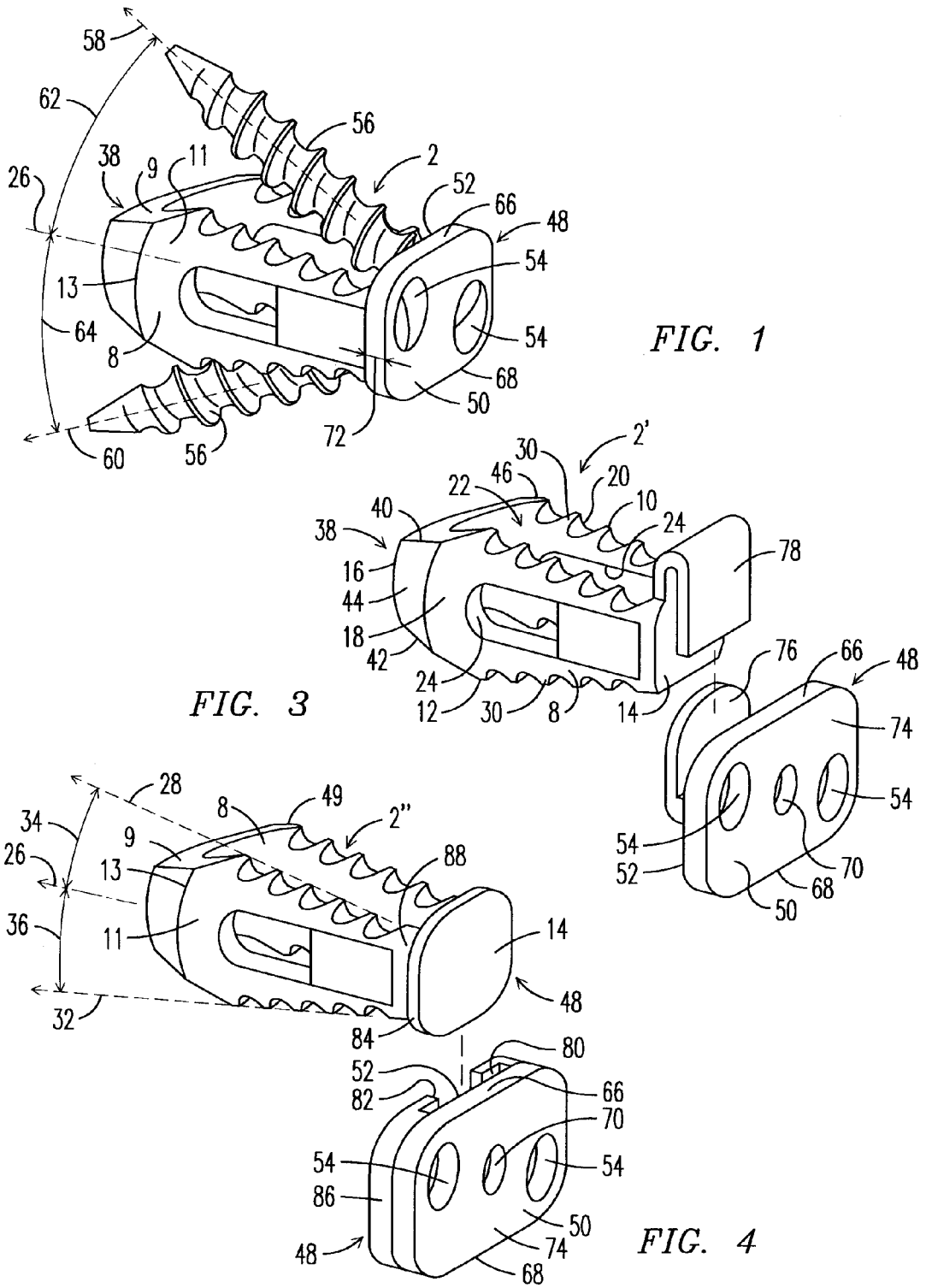

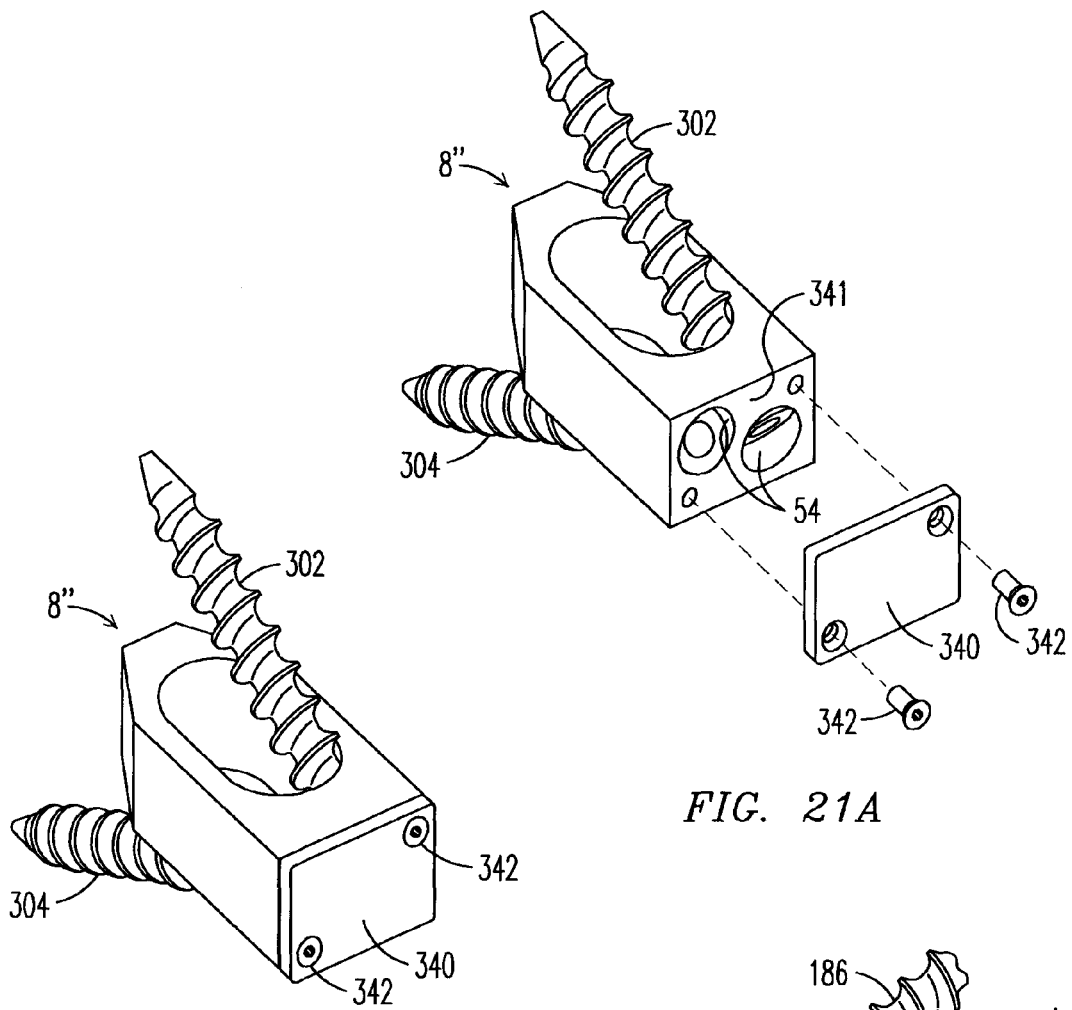
FIG. 21A
FIG. 21B
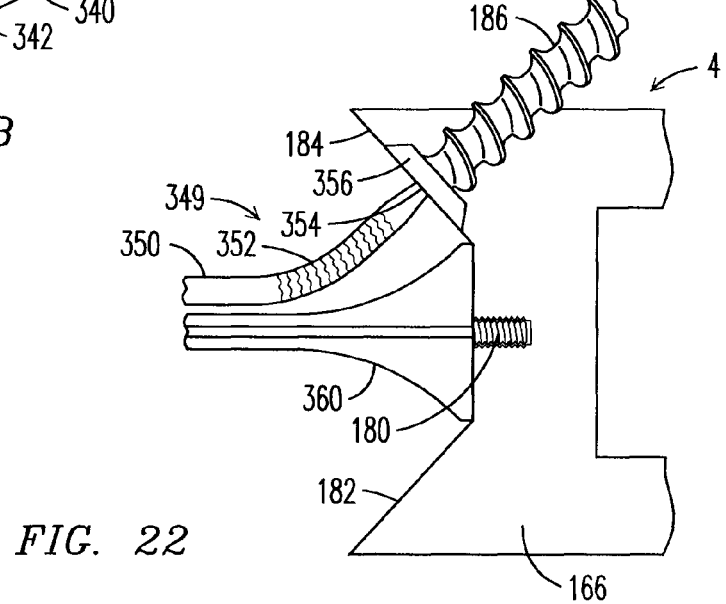
FIG. 22

US 8,641,765 B2

POSTERIOR SPINAL IMPLANT SYSTEM

CROSS REFERENCE TO RELATED APPLICATION

Priority is hereby claimed to the filing date of U.S. provisional patent application Ser. No. 61/233,246 filed on Aug. 12, 2009 and U.S. provisional patent application Ser. No. 61/315,531 filed on Mar. 19, 2010.

INCORPORATION BY REFERENCE

The entire disclosure of U.S. provisional patent application Ser. No. 61/233,246 and the entire disclosure of U.S. provisional patent application Ser. No. 61/315,531 are incorporated herein in their entirety by this reference.

FIELD OF THE DISCLOSURE

The present invention generally relates to a spinal implant to be inserted into an inter-vertebral space, thereby supporting a portion of a spinal column of a patient. Specifically, the disclosure relates to a spinal implant system that may be installed into the inter-vertebral space via: a posterior side of the inter-vertebral space; a posterior-lateral side of the inter-vertebral space, and an oblique side of the inter-vertebral space, and method for installing the spinal implant system.

BACKGROUND OF THE DISCLOSURE

The spinal column, which is the central support to the vertebrate skeleton and a protective enclosure for the spinal cord, is a linear series of bones, or vertebrae. Inter-vertebral discs separate and reduce friction between adjacent vertebrae and absorb compression forces applied to the spinal column. Spinal nerves that extend from each side of the spinal cord exit the column at inter-vertebral forama.

A typical vertebra comprises an anterior body, and a posterior arch that surrounds the spinal cord lying within the vertebral foramen formed by the arch. The muscles that flex the spine are attached to three processes extending from the posterior arch. On the upper surface of each vertebra in a standing human are two superior articulated processes that oppose two inferior articulated processes extending from the lower surface of an adjacent vertebra. Facets on the opposing processes determine the range and direction of movement between adjacent vertebrae, and hence the flexibility of the spinal column.

Back pain is one of the most significant problems facing the workforce in the United States today, is a leading cause of sickness-related absenteeism, and a major cause of disability for people between the ages of 19 and 45. Back pain can occur from pinching or irritating a spinal nerve, compression of the spine, vertebral shifting relative to the spinal cord axis, and formation of bone spurs. The most common cause of disabling back pain, however, generally stems from trauma to a vertebral disc, such as from mechanical shock, stress, tumors, or degenerative diseases. In many cases, the disc can become permanently damaged or degenerated, such that the preferred treatment necessitates partial or total excision and replacement of the damaged disc.

Traumatic injury to a vertebral disc that is not removed frequently can promote scar tissue formation. Such scar tissue typically is thicker than the healthy tissue, such that the disc continues to progressively degenerate, lose water content, and can stiffen and become significantly less effective as a shock absorber. Eventually, the disc can deform, herniate, or collapse, eliminating the flexibility of the spinal column, and potentially leading to further degeneration or damage to other vertebral discs of the spinal column. At such a point, the only option is for the damaged disc to be partially or completely removed. When the disc is partially or completely removed, generally it is necessary to replace the excised material to prevent direct contact between the boney surfaces of the adjacent vertebrate on either side of the removed disc. For example, a vertebral spacer is inserted between adjacent vertebrate to provide restorative force and function as a shock absorber between the adjacent vertebrate. Another alternative approach has been to insert a "cage" that can maintain a space occupied by the removed disc to prevent the vertebrate from collapsing and impinging upon the nerve roots of the spine. Still further, spinal fusion has been used to restrict motion and stabilize patients' spines by fusing adjacent vertebrate together. This generally can reduce mechanical back pain by preventing the now immobile vertebrate from impinging on a spinal nerve; however, such stability and pain reduction generally is created at the expense of spinal flexibility and motion.

Thus, many conventional techniques for disc repair and replacement can be limited in terms of their size or configuration of the implant and thus generally are not designed to accommodate variations in size of the gap resulting from the excising of the vertebral disc material. However, conventional techniques often require installation of an implant through the patients front side, or anterior, or require a larger surgical opening be placed in the patients back to introduce a traditional rod and pedicle screw system. Installation of the traditional systems may require the dissection of muscles, undergoing a surgical procedure lasting long in duration, extensive blood loss during surgery, increased risk of nerve damager to the patient and oftentimes increasing the patient's recovery time.

SUMMARY

Generally, the present disclosure provides an improved spinal implant, wherein the spinal implant may be an implant spacer body, a plate, or a combined implant spacer body and plate implant. The spinal implant may allow, or prevent, motion in a joint, such as the joint established by adjacent vertebrae in a spinal column. The spinal implant has at least an advantage of being installable through a patients posterior, lateral, oblique, or posterior-lateral relative to the spine and also has the advantage of avoiding use of a pedicle rod system for placement of screws and instead uses the vertebral body to support the screws. Further, the spinal implant as disclosed may be installed from the smaller side of a disk. Thus, the bone screws and the spinal implant replaces the traditional pedicle screws and the rod, thereby avoiding the more difficult task of identifying the pedicles and screw placement.

Briefly described, one embodiment of a spinal implant that is installed in an inter-vertebral space from a posterior of a patient comprises an implant spacer body that defines an upper surface, a lower surface, a posterior surface, and an anterior surface. At least one of the upper surface or the lower surface partially tapers from the anterior surface to the posterior surface at a predetermined first angle with respect to an implant spacer body centerline. A plate may be mechanically connected to the implant spacer body. The plate has a plate posterior surface and a plate anterior surface with the plate anterior surface arranged adjacent the body posterior surface.

The plate further defines at least two screw passages extending through the plate, from the plate posterior surface to the plate anterior surface. Each screw hole may be oriented at a predetermined second angle with respect to the implant spacer body centerline. A screw may be received by each of said screw passages, each of said screws extending through said plate, from said plate posterior to said plate anterior.

In another embodiment, inter-vertebral spacer comprises a three-dimensional wedge shaped spacer component that is arranged within an inter-vertebral space between two adjacent vertebrae. The spacer component extends from a posterior of the inter-vertebral space toward an anterior of the inter-vertebral space.

The spacer component has an upper surface arranged proximate an upper vertebrae end plate and a lower surface arranged proximate a lower vertebrae end plate such that the upper surface and the lower surface of the spacer component taper to a spacer component thin edge, from the anterior to the posterior.

A plate component is attached to the spacer component thin edge and the plate component defines at least two screw passages that diverge. A first screw passage extends through said plate component toward said upper surface and a second screw passage extends through said plate toward said lower surface. A screw received by each screw hole and each of the screws extend from the posterior toward the anterior and into either said upper vertebral end plate or said lower vertebral end plate. The spacer component, and a screw head of each of said screws, and the plate component reside within the inter-vertebral space.

In yet another embodiment, a method of posterior installation of an implant into an inter-vertebral space between adjacent vertebrae in a spinal column comprises the steps of:

(a) arranging a patient so their posterior is surgically accessible;

(b) creating a surgical incision to gain access to said patient's spinal column;

(c) removing a damaged vertebral disk between adjacent vertebrae to create an inter-vertebral space;

(d) installing said implant in said inter-vertebral space, said implant contacting an end plate of each of said adjacent vertebrae such that a thin end of a wedge shaped spacer of said implant is arranged toward said posterior, said thin end of said wedge shaped spacer connected to a plate portion of said implant, said plate portion having at least two screw passages extending therethrough; and (e) inserting a screw through each of said screw passages such that said screws are installed in said end plates of said vertebrae while said wedge shaped implant is arranged within said inter-vertebral space.

In another embodiment, a spinal implant comprises a spacer component having an upper surface and a lower surface, such that at least one of the upper surface and/or the lower surface taper from an anterior to a posterior. The upper surface contacts a first bone plate of a first vertebrae and the lower surface contacts a second bone plate of a second vertebrae and at least one bone screw passage is arranged in the spacer and oriented to direct a bone screw into either the first vertebrae or the second vertebrae.

In still yet another embodiment, an inter-vertebral implant comprising a plate having an upper surface and a lower surface. At least one bone screw passage is arranged in the plate and oriented to direct a bone screw into either the first vertebrae or the second vertebrae to secure the plate in an inter-vertebral space.

Additional features and advantages will be set forth in the detailed description which follows, and in part will be readily apparent to those skilled in the art from that description or recognized by practicing the embodiments as described herein, including the detailed description which follows, the claims, as well as the appended drawings.

It is to be understood that both the foregoing summary and the following detailed description are merely exemplary of preferred embodiments, and are intended to provide an overview or framework to understanding the nature and character of the claims. The accompanying drawings are included to provide a further understanding, and are incorporated in and constitute a part of this specification. The drawings illustrate the exemplary embodiments, and together with the description serve to explain principles and operation of the various embodiments.

BRIEF DESCRIPTION OF THE DRAWINGS

According to common practice, the various features of the drawings discussed below are not necessarily drawn to scale. Dimensions of various features and elements in the drawings may be expanded or reduced to illustrate more clearly the embodiments of the disclosure.

FIG. 1 is an isometric view of a spinal implant that is generally installed from a posterior side of an inter-vertebral space according to a first embodiment of the disclosure.

FIG. 3 is an isometric view of a spinal implant that is generally installed from a posterior side of an inter-vertebral space according to another embodiment of the disclosure.

FIG. 4 is an isometric view of a spinal implant that is generally installed from a posterior side of an inter-vertebral space according to another embodiment of the disclosure.

FIG. 21A and FIG. 21B are isometric views of a plate type locking device.

FIG. 22 is a side view of a bone screw installation tool for use with a spinal implant as disclosed herein and a bone screw as disclosed herein.

DETAILED DESCRIPTION

Figure 2A:
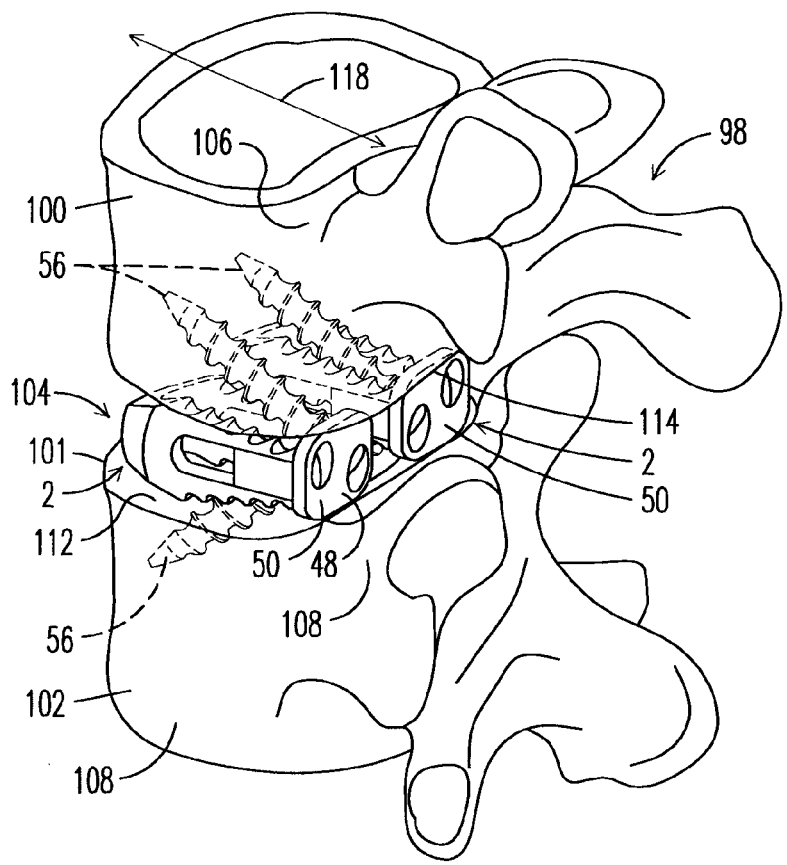
FIG. 2A is an isometric view of a pair of spinal implants according to FIG. 1 illustrated in situ between adjacent vertebrae in an inter-vertebral space.

Referring now in more detail to the drawing figures, wherein like reference numerals indicate like parts throughout the several views, FIGS. 1, 3 and 4 are isometric views of a spinal implant 2, 2', 2" for an inter-vertebral space according to several embodiments of the disclosure. The spinal implant 2, 2', 2" may generally be comprised of an implant spacer body 8 and a plate 48. Generally, the implant spacer body 8 of FIGS. 1, 3, 4 and 5 is similar in construction and will be discussed collectively herein. In some embodiments (see FIGS. 7 and 8, for example), the spinal implant may be comprised of an implant spacer body 8 only. In other embodiments, the spinal implant 2, 2', 2" may be comprised of a plate 48 only. And in still other embodiments (FIGS. 1, 3 and 4, for example), the spinal implant 2, 2', 2" may be comprised of both an implant spacer body 8 and a plate 48. As illustrated in FIGS. 1, 3 and 4, the spinal implant 2, 2', 2" is comprised of an implant spacer body 8 and a plate 48.

Generally, the spinal implant 2, 2', 2" is for insertion into an inter-vertebral space, or gap between adjacent vertebrae of a patient's spine to replace substantially all of a vertebral disc or vertebrae that has been excised or removed due to damage or degeneration of the disc. The spinal implant of the present disclosure may also be useful to replace a vertebral disc that has degenerated due to traumatic injury, vertebral displacement, disease (i.e., autoimmune disease, rheumatoid arthritis, etc.), or any other pathological condition of the spinal column that may injure or shift the inter-vertebral discs. The spinal implant of the present disclosure also provides support to the adjacent vertebrae of the patient's spine to help maintain the separation between the vertebrae, while also preserving the natural curvature of the spine and further enabling regenerative bone growth and adjustment of the inter-vertebral spacing between the adjacent vertebrae to accommodate growth or expansion therebetween. For spinal applications, for example, the length of the sides or edges of the spinal implant 2, 2', 2" may range anywhere from 0.5 millimeters (mm) to 5 mm and may at least depend on the length and size of the inter-vertebral spacing between the adjacent vertebrae. Generally, the spinal implant 2, 2', 2" may be inserted into the inter-vertebral space between adjacent vertebrae from the posterior of a patient. However, the spinal implant 2, 2', 2" as disclosed also provides the flexibility of being installed through a patients posterior, lateral, oblique, or posterior-lateral positions relative to the spine, if necessary.

The spinal implant 2, 2', 2" generally may comprise an implant spacer body 8 and a plate 48. The implant spacer body 8 may comprise an introduction portion 9, which is a portion of the implant spacer body 8 that facilitates installation of the spinal implant 2, 2', 2". The implant spacer body 8 may also comprise an fusion portion 11, which is a portion of the implant spacer body 8 that promotes fusion of the spinal implant 2, 2', 2" with adjacent vertebrae. The implant spacer body 8 transitions from the introduction portion 9 to the fusion portion 11 at a transition location 13. Generally, the introduction portion 9 may taper from the transition location 13 to an anterior surface 16 and the fusion portion 11 may taper from the transition location 13 to a posterior surface 14. The term "taper" used throughout this document is understood by the skilled artisan to mean become thinner or narrower at one end. For example, the fusion portion 11 tapering from the transition location 13 to the posterior surface 14 means that the fusion portion 11 becomes thinner or narrower at, or near, the posterior surface 14. Additionally, it is understood that the term taper may mean a linear taper, a nonlinear taper, or a compound taper (i.e. a taper comprised of several lengths of differing taper). Furthermore, it is understood that the entire surface need not taper. For example, the fusion portion 11 of the implant spacer body 8 may taper anywhere from 10%-90% of a length (i.e. a distance from the transition location 13 to the posterior surface 14 as measured along an implant body centerline 26) of the fusion portion 11.

The spinal implant 2, 2', 2" may be a single piece construction, as illustrated in FIG. 1, wherein the implant spacer body 8 and the plate 48 are fabricated as a single structure. In other embodiments, the implant spacer body 8 and the plate 48 may be fabricated as separate components, such as the embodiments illustrated in FIGS. 3 and 4, and connected to each other, or attached to each, other using any suitable means. Several suitable means are discussed herein.

The implant spacer body 8 may be a three dimensional wedge shaped body having a hollow central cavity 22. The hollow central cavity 22 may improve a weight to strength ratio of the implant spacer body 8 as well as improve the weight to strength ratio of the spinal implant 2, 2', 2". It is not required that the implant spacer body 8 have a hollow central cavity 22. The spinal implant 2, 2', 2" may comprise a posterior end and an anterior end. The posterior end of the spinal implant 2, 2', 2" is located toward the patient's posterior and the anterior end of the spinal implant 2, 2', 2" is located toward the patient's anterior. The anterior and posterior ends of the spinal implant 2, 2', 2" need not be parallel. Generally, when the spinal implant 2, 2', 2" is installed, the posterior end will be arranged proximate a posterior of a vertebrae and the anterior end will be arranged proximate an anterior of the vertebrae.

The fusion portion 11 of the implant spacer body 8 generally has an upper surface 10 and a lower surface 12. The upper surface 10 and lower surface 12 may contact upper and lower vertebral bone plates (see FIG. 10B), respectively. The implant spacer body 8 comprises the anterior surface 16 and the posterior surface 14. The implant spacer body 8 further comprises a first side surface 18 and a second side surface 20. The upper surface 10 and lower surface 12, the posterior surface 14 and anterior surface 16, and the first side surface 18 and the second side surface 20 of the implant spacer body 8 will define an exterior envelope of the implant spacer body 8. The implant spacer body 8 may have openings 24 arranged in the first side surface 18 and the second side surface 20 that extend to the central cavity 22. The openings 24 at least allow bone material to be placed in the central cavity 22 and aid in fusing the spinal implant 2, 2', 2" to the adjacent vertebrae.

The introduction portion 9 may have an anterior end taper 38 that is arranged proximate the anterior surface 16 of the implant spacer body 8. The implant spacer body 8 may taper from a maximum height location 49 (as measured in a direction from the upper surface 10 to the lower surface 12) to the anterior surface 16 of the implant spacer body 8. Furthermore, the implant spacer body 8 may taper from the first side surface 18 and/or the second side surface 20 toward the anterior surface 16. The anterior end taper 38 is comprised of an anterior end upper surface taper 40, an anterior end lower surface taper 42, an anterior end first side surface taper 44, and an anterior end second side surface taper 46 and the anterior end is part of the introduction portion 9. These four surfaces 40, 42, 44, 46 taper to the anterior surface 16 of the implant spacer body 8 and reduce the size of the anterior end 16 to create a tip. This facilitates installation of the spinal implant 2, 2', 2" into the inter-vertebral space.

The implant body centerline 26 of the implant spacer body 8 is located along a bilateral axis of symmetry of the implant spacer body 8. The upper surface 10 has an upper surface taper axis 28 and the lower surface 12 has a lower surface taper axis 32. The upper surface taper axis 28 and lower surface taper axis 32 are such that the upper surface 10 may taper from proximate the anterior end 16 to the proximate the posterior end 14 and the lower surface may taper from proximate the anterior end 16 to proximate the posterior end 14, respectively. A predetermined first taper angle 34 establishes an amount of taper angle for the upper surface 10 and a predetermined third taper angle 36 establishes an amount of taper angle for the lower surface 12. The predetermined first taper angle 34 may range from 0 to 25 degrees and the predetermined third taper angle 36 may range from 0 to 25 degrees. There is no requirement that the value of the predetermined first taper angle 34 and the predetermined third taper angle 36 be the same value, and in some embodiments the upper surface 10 may taper and the lower surface 12 may not taper, or vice-versa. The value of the taper angle 34, 36 may in part depend on the amount of bone plate of the upper or lower vertebrae required to be removed during the installation process. The implant spacer body 8 tapering from the anterior surface 16 to the posterior surface 16 at least improves the fit and interface between the spinal implant 10 and respective bone plates of adjacent vertebrae by more closely following a natural contour of the bone plates.

A plurality of "teeth" 30 or serrations 30 may be arranged on the upper surface 10 and/or the lower surface 12 of the implant spacer body 8. The teeth 30 at least function to help secure the spinal implant 2, 2', 2" in a desired position in the inter-vertebral space between adjacent vertebrae.

The implant spacer body 8 may have a thickness that is substantial to support anticipated mechanical loading and unloading during use. This may include designing and/or sizing the implant spacer body 8 to account for any low cycle fatigue concerns that may arise during a lifetime of cyclical loading and unloading of the spinal implant 2, 2', 2".

The spinal implant 2, 2', 2" may further comprise a plate 48. The plate 48 may be arranged proximate the posterior surface 14 of the implant spacer body 8. The plate 48 may have a plate posterior surface 50 and a plate anterior surface 52. In some embodiments, the plate posterior surface 50 may be the posterior end of the spinal implant 2. The plate has an upper surface 66 and a lower surface 68. The upper surface 66 and lower surface may comprise a plurality of teeth or serrations, which at least provide further support between the plate 48 and adjacent vertebrae as well as further improve contact and/or improve the connection between the plate 48 and vertebrae. The plate 48 is illustrated as being generally rectangular in shape but may be any shape necessary that may be required for installation or function (i.e. to support a portion of a load carried by the spinal column). For example, the plate 48 may have a plate profile 74 that may be rectangular, triangular, circular, arcuate, elliptical, polygonal, or combinations thereof. Any geometric shape for the plate 48 may suffice as long as the plate 48 may at least function as intended. The plate profile 74 may be dictated by several factors, including manufacturing capabilities, magnitude of load to be supported, ease of assembly and installation, and/or location of installation. It will be known by the skilled artisan that other factors exist and the factors listed are merely exemplary. Although not illustrated, the plate posterior surface 50 may be concave with the anterior surface 52 being substantially flat. A concave surface may provide for easier installation of the spinal implant 2, 2', 2" because at a minimum, a bone screw head (see FIG. 17B) may be below the concave surface when installed.

The plate 48 may comprise at least one bone screw passage 54. In general, the plate 48 may comprise at least 2 bone screw passages 54 for stability purposes. In some embodiments, there may be three bone screw passages 54 while other embodiments may comprise four bone screw passages 54. Each bone screw passage 54 is meant to accommodate a single bone screw (see FIGS. 2A and 2B). The bone screw passages 54 may be oriented at a predetermined second angle 62, measured relative to a bone screw axis 58 and the implant spacer body centerline 26, and a predetermined fourth angle 64, measured relative to a bone screw axis 60 and the implant spacer body centerline 26. The predetermined second angle 62 and the predetermined fourth angle 64 may be greater in measure than the predetermined first angle 34, and/or the predetermined third angle 36. The predetermined second angle 62 and the predetermined fourth angle 64 should be sufficient in measure to promote directing a bone screw into an adjacent vertebrae to sufficiently anchor the spinal implant 2, 2', 2" to the vertebrae. The measures of the predetermined second angle 62 and the predetermined fourth angle 64 may each range from 0 to 45 degrees. For the embodiments disclosed in FIGS. 1, 3 and 4, the bone screw passages 54 may be arranged in the plate 48 so installation of a bone screw is facilitated (e.g. proximate opposite corners of the plate 48). Generally, the plate 48 of the spinal implant 2', 2" may have at least one through hole 70 arranged near a center of the plate 48. The through hole 70 may accommodate a support tool or installation tool (not shown), which facilitates installation of the spinal implant 2', 2". In some applications, the bone screw, or other attachment, can be placed through the central through hole and attach the plate 48 to the implant spacer body 8. The plate 48 may have a plate thickness 72 (i.e. the distance between the plate posterior surface 50 and the plate anterior surface 52) sufficient to support a load developed in the inter-vertebral space as a result of normal everyday activity by the patient as well as extreme loading conditions. The plate 48 may also have a sufficient thickness 72 to maintain the inter-vertebral space between adjacent vertebrae.

The bone screw passage 54 may be countersunk or recessed to allow a screw head of the bone screw to reside below the posterior surface 50 of the plate 48 and not project into a posterior of the spinal column (see FIG. 17B). The screw head may be larger than the bone screw passage 54. This may allow the bone screw to secure the spinal implant 2, 2', 2" to the adjacent vertebrae.

Any bone screw can be used and the bone screw can be selected to satisfy installation needs, such as bone screw length, bone screw diameter, bone screw head diameter, and bone screw material to name but a few. It is anticipated that at least one screw will be used to affix the spinal implant 2, 2', 2" to each vertebrae. Thus, a minimum of two bone screws, one bone screw through the spinal implant 2, 2', 2" and into an upper vertebrae, and one bone screw through the spinal implant 2, 2', 2" and into the lower vertebrae, may be necessary to anchor the spinal implant 2, 2', 2" between adjacent vertebrae. An oval or elliptical screw passage 54 may allow the bone screw to "pivot" in an upward or downward direction relative to the plate implant and permit installation of the bone screw into the vertebrae at a variety of angles. A semi-constrained poly-axial screw (see FIG. 18B) may be used as well and may also allow the bone screw to "pivot" in an upward or downward direction. It is also anticipated that when installed, the posterior surface of the plate implant will be at least below with the posterior surfaces of the adjacent vertebrae, if not slightly below the posterior surfaces of adjacent vertebrae. It is preferred that no portion of the spinal implant (i.e. the implant spacer body, the plate, the bone screws, and the bone screw head) extend beyond the inter-vertebral space or the posterior surfaces of the adjacent vertebrae (see FIGS. 2A, 2B and 5B).

FIGS. 3 and 4 show alternate embodiments of the spinal implant 2', 2". In the embodiment of FIG. 3, the plate 48 and the implant spacer body 8 are separate components and may at least be connected by an engagement between a plate "U" shaped connector 76 and a implant spacer body "U" shaped connector 78. When the plate "U" shaped connector 76 engages the implant spacer body "U" shaped connector 78, the plate 48 and the implant spacer body 8 become connected to each other and are able to function as the spinal implant 2'. The central passage 70 is arranged in the plate 48. A securing means, such as a screw, a pin, a bolt, or a pin, to name but a few, may extend through the central hole 70 and contact the implant spacer body "U" shaped connector 78 and partly secure the plate 48 to the implant spacer body 8. The central passage 70 may be countersunk if necessary so the securing means is flush with, or below, the plate posterior surface 50.

FIG. 4 shows an alternate means of attaching the plate 48 to the implant spacer body 8. Plate 48 comprises a slot 80 that is arranged in a backing 86 that may be attached to the plate anterior surface 52. A channel 82 may be located in the backing and permits a neck 88 of the implant spacer body to slide into the backing 86 and the implant spacer body 8 to engage with the plate 48. A flange 84 may be arranged proximate the posterior surface 14 and slidably engages the slot 80 of the plate 48. A central passage 70 is arranged in the plate 48. A securing means, such as a screw, a pin, a bolt, or a rod, to name but a few, may extend through the central hole 70 and contact the flange 84 and partly secure the plate 48 to the implant spacer body 8.

The "U" shaped connector shown in FIG. 3 and the slot connector shown in FIG. 4 are but a few of the available attachment means to connect or attach the plate 48 with the implant spacer body 8 and the attachment means of FIGS. 3 and 4 are not meant to be limiting. For example, a screw or pin may be a suitable attachment means, a flexible member may be a suitable attachment means, or an adhesive material may be a suitable attachment means.

Figure 2B:
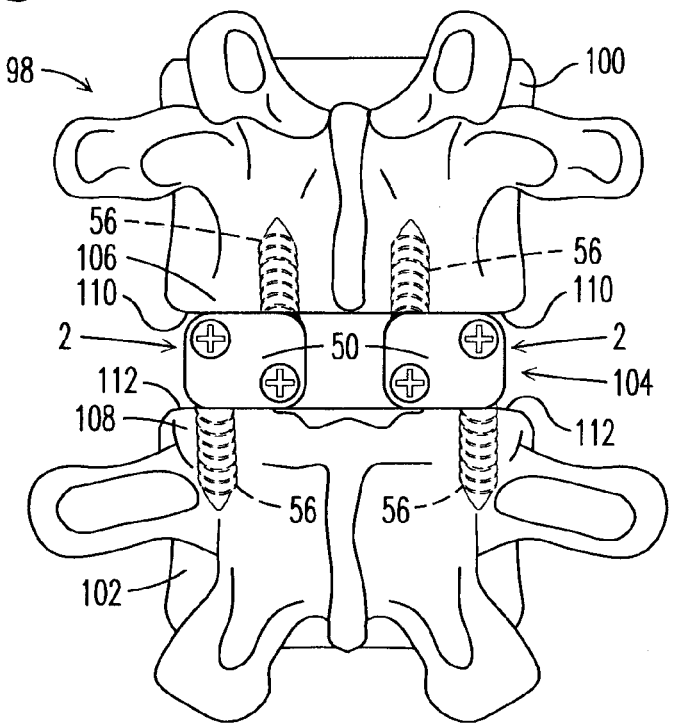
FIG. 2B is an illustration of the pair of spinal implants of FIG. 2A when viewed from a posterior side looking toward an anterior side of adjacent vertebrae

FIGS. 2A and 2B are an isometric view and a rear view, respectively, of a posterior portion 98 of a portion of a spinal column and show the spinal implant of any of the embodiments discussed herein in an installed configuration. For convenience, the following discussion will be limited to the embodiment of the spinal implant 2 of FIG. 1, but it is understood that the disclosure is not limited to the embodiment of spinal implant 2. The posterior 98 of a spine is illustrated and a pair of spinal implants 2 are arranged in an inter-vertebral space 104 between adjacent vertebrae 100, 102. An upper vertebrae 100 and a lower vertebrae 102 each have a posterior surface 106, 108 respectively. Although the spinal implant 2 is illustrated as substantially aligned along a posterior to anterior axis 118, the skilled artisan will understand that depending on how the spinal implant 2 is installed, the spinal implant may be skewed with the posterior to anterior axis 118 (see FIGS. 9A and 9B). For example, if the spinal implant 2 is installed from a posterior-lateral side of the inter-vertebral space 104, the spine implant 2 will be skewed relative to the posterior to anterior axis 118. It is anticipated that the spinal implant 2 may be installed via the posterior, lateral, or posterior-lateral positions relative to the inter-vertebral space 104. When installed, the anterior surface of the implant spacer body 8 may be arranged proximate an anterior 101 of the vertebrae 100, 102 and the posterior surface 50 of the plate 48 arranged toward the posterior 98 of the vertebrae 100, 102. The serrations 30 of the upper surface 10 may contact an upper vertebrae bone plate 110 and serrations 30 of the lower surface 12 may contact a lower vertebrae bone plate 112. If the plate upper surface 66 and plate lower surface 68 comprise serrations, they will also contact the upper and lower bone plates 110, 112 respectively.

Figure 5A:
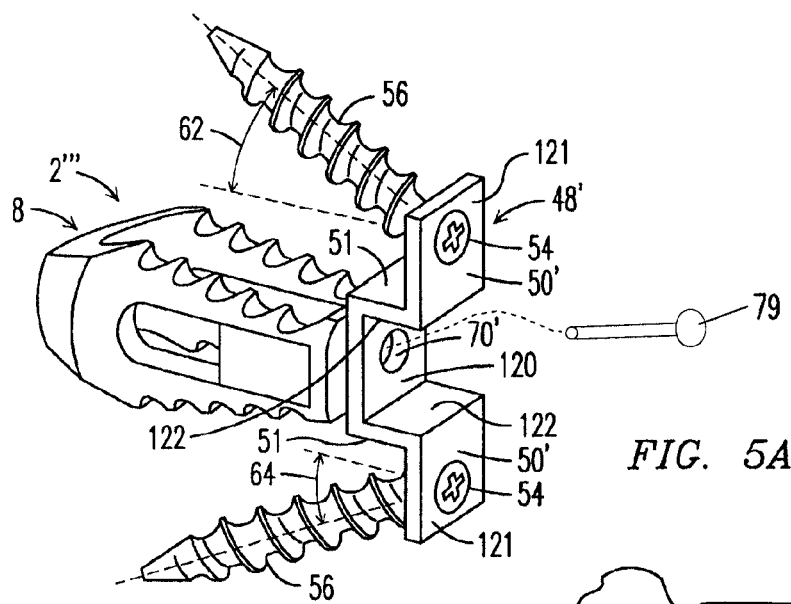
FIG. 5A is an isometric view of a spinal implant that is generally installed from a posterior side of an inter-vertebral space according to another embodiment of the disclosure.
Figure 5B:
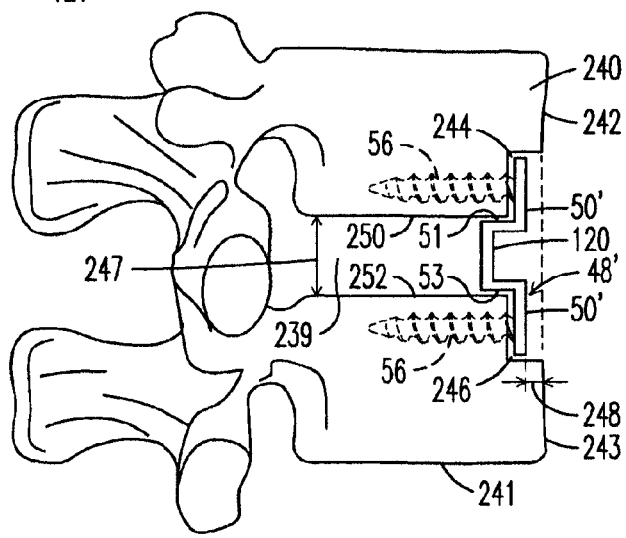
FIG. 5B is a side view of the spinal implant of FIG. 5A illustrating the spinal implant in-situ and bone screws at a different orientation.

When the spinal implant 2 is installed, regardless of whether the spinal implant 2 is comprised of only an implant spacer body 8, or only a plate 48, or an implant spacer body 8 and a plate 48, the spinal implant posterior end (i.e. the plate posterior surface 50 for this particular spinal implant 2) will be arranged interior to the upper vertebrae posterior surface 106 and the lower vertebrae posterior surface 108 (see FIG. 5B for clarity). Furthermore, the heads of the bone screws 56 may be interior to the upper vertebrae posterior surface 106 and the lower vertebrae posterior surface 108. It is generally preferred that no portion of the spinal implant 2 protrude beyond the upper vertebrae posterior surface 106 and the lower vertebrae posterior surface 108. In the installed configuration, the spinal implant should be at least 4 mm from the spinal cord (not shown) and nerve bundles extending from the spinal cord. The posterior surface 106 of the upper vertebrae 100 and the posterior surface 108 of the lower vertebrae 102 establish a substantially vertical plane (not shown) extending across the inter-vertebral space 104. It is intended that the spinal implant 2 be installed such that when installation is complete, no portion of the spinal implant 2 (including the implant spacer body 8, the plate 48, and the bone screws 56) will extend beyond the plane. In some embodiments, it may be preferred that the spinal implant be installed to reside entirely within the inter-vertebral space 104 such that when installed the spinal implant does not extend beyond a plane established between a perimeter of an end of the upper vertebrae 100 adjacent the spinal implant and a perimeter of an end of the lower vertebrae 102 adjacent the spinal implant.

It can be seen that the bone screws 56 extend into the adjacent vertebrae and assist in securing the spinal implant 2 in place. As illustrated, a total of four bone screws 56 are used to secure the spinal implants 2 in place. In FIG. 2B, the bone screws 56 in the lower bone screw passage 54 are illustrated as extending through the lower bone screw passage 54 to the upper vertebrae 100 and the bone screws 56 in the upper bone screw passage 54 are illustrated as extending through the upper bone screw passage 54 to the lower vertebrae 102. This is but one configuration and it would be acceptable for the bone screws 56 in the lower bone screw passage 54 to extend through the lower bone screw passage 54 to the lower vertebrae 102 and the bone screws 56 in the upper bone screw passage 54 to extend through the upper bone screw passage 54 to the upper vertebrae 100. As discussed in this disclosure, if desired, each spinal implant 2 may be held in place by fewer or more bone screws 56 and the number of bone screws 56 required may at least depend on the application, the location in the spinal column the implant is being placed, and the size of the bone screws 56 being used. Further, two spinal implants 2 are illustrated in the inter-vertebral space 104. If necessary, a single implant 2 may be used.

FIG. 5A shows a spinal implant 2''' according to another embodiment of the disclosure. The spinal implant 2''' comprises a implant spacer body 8 and a plate 48'. However, in some embodiments, the spinal implant 2''' may be comprised of the implant spacer body 8 only, or the plate 48' only, or the implant spacer body 8 and the plate 48'. The plate 48' may have at least one through hole 70' arranged near a center of the plate 48'. A securing means 79, such as a screw, a pin, a bolt, or a rod, to name but a few, may extend through the central hole 70' and partly secure the plate 48' to the implant spacer body 8. The plate 48' is generally channel shaped having a substantially flat, recessed plate portion 120, two legs 122, and two flange portions 124. The flange portions 124 each a have a posterior surface 50' and the legs 122 each have an outer surface 51. The flange portions 122 each have a screw passage 54, which extends from the posterior surface 50' through the flange portions 122. A bone screw 56 may extend through the bone screw passage 54 and assist in securing the spinal implant 2''' to adjacent vertebrae. The bone screw passages 54 may be oriented at a predetermined second angle 62, measured relative to a bone screw axis 58 and the implant spacer body centerline 26, and a predetermined fourth angle 64, measured relative to a bone screw axis 60 and the implant spacer body centerline 26. The predetermined second angle 62 and the predetermined fourth angle 64 should be sufficient in measure to promote directing a bone screw 56 into the adjacent vertebrae. The measures of the predetermined second angle 62 and the predetermined fourth angle 64 may each range from 0 to 45 degrees.

FIG. 5B shows the spinal implant 2''' installed in an inter-vertebral space, wherein the spinal implant 2''' is comprised of the plate 48' only. Outer surface 51 of the plate 48' contacts an upper bone plate 250 of an upper vertebrae 240 and outer surface 51 contacts an lower bone plate 252 of a lower vertebrae 241. Upper vertebrae 240 has a posterior surface 242 and lower vertebrae 241 has a posterior surface 243. An upper cavity 244 may be established in the upper vertebrae 240 by removing bone and a lower cavity 246 may be established in the lower vertebrae 241 by removing bone. Cavities 244 and 246 may be required so the posterior surface 50' of the plate 48' is interior to the posterior surface 242 of the upper vertebrae 240 and interior to the posterior surface 243 of the lower vertebrae 241. The use of cavities in adjacent vertebrae, such as those described herein, may be used for the installation of any spinal implant disclosed herein. A width of the channel 120 may be increased or decreased to maintain a distance 247 between adjacent vertebrae 240 241 of the inter-vertebral space 239. A concept of the disclosure is that no portion of the posterior surface of the plate 48', including the screw heads of the bone screws 56, will protrude beyond the posterior surfaces 242, 243 of the vertebrae 240, 241. This concept may be extended and applied to any of the spinal implant embodiments disclosed herein.

Figure 6:
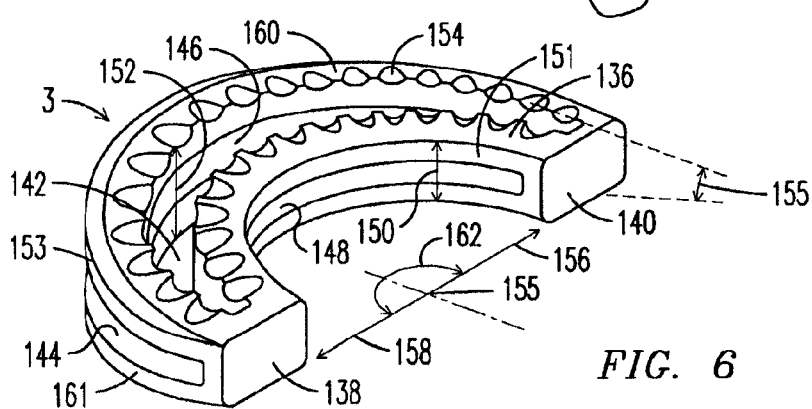
FIG. 6 is an isometric view of a spinal implant that is generally installed from a posterior side of an inter-vertebral space according to another embodiment of the disclosure.

FIG. 6 shows a spinal implant 3 according to another embodiment disclosed herein. The spinal implant 3 is essentially an implant spacer body and generally does not include a plate. However, if necessary, a plate may be included. The spinal implant 3 has an implant body 136 having a first end 138 and a second end 140, the first end 138 and the second end 140 establishing a posterior end of the implant. The spinal implant has an upper surface 160, a lower surface 161, an inner surface 151 and an outer surface 153. An envelope of the implant body 136 is defined by the upper and lower surfaces 160, 161, the first and second ends 138, 140, and the inner and outer surfaces 151, 153. A plurality of channels 142, 144, 146, 148 are arranged in the implant body 136 and may receive bone material when the spinal implant 3 is installed. The bone material fuses with bone material of adjacent vertebrae and better secures the spinal implant 3 to the vertebrae. The implant body 136 may comprise a plurality of serrations 154 arranged on the upper surface 160, the lower surface 161, or the upper and lower surfaces 160, 161. The inner surface may have a inner surface height 150 and the outer surface may have an outer surface height 152. The spinal implant 3 tapers from the outer surface 153 to the inner surface 151 at a taper angle 155. The taper may be a linear taper as illustrated or a non-linear taper. Further, the upper surface 160 only may taper, the lower surface 161 only may taper, or both the upper and lower surfaces 160, 161 may taper. A non-linear taper may include a plurality of continuous tapers that vary in degree of taper.

Bone screw passages (not shown) are arranged at the first and second ends 138, 140. Typically, two bone screw passages may be arranged at each end 138, 140, with a total of four bone screws securing the spinal implant 3 to the adjacent vertebrae. The bone screw passages may be countersunk to allow a bone screw head to reside within the countersunk portion.

The spinal implant 3 is illustrated as being semi-circular but is not required to be semi-circular. An implant body angle 162 establishes an angular measure between the first and second ends 138, 140. Reference axis 1 and reference axis 2 extend from an implant body center 155 toward the first and second ends 138, 140, respectively. The implant body angle 162 is the angular measure between the reference axis 1 and reference axis 2.

The spinal implant 3 may be installed in an inter-vertebral space by bringing the first or second end 138, 140 of the spinal implant 3 proximate one side of the inter-vertebral space and rotating the spinal implant into position in the inter-vertebral space. When in position, the first and second ends 138, 140 of the spinal implant 3 may not extend beyond the posterior surfaces of the vertebrae.

Figure 7:
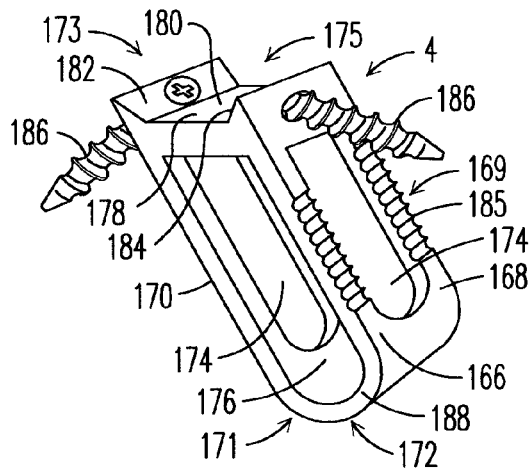
FIG. 7 is an isometric view of a spinal implant that is generally installed from a posterior side of an inter-vertebral space according to another embodiment of the disclosure.
Figure 8:
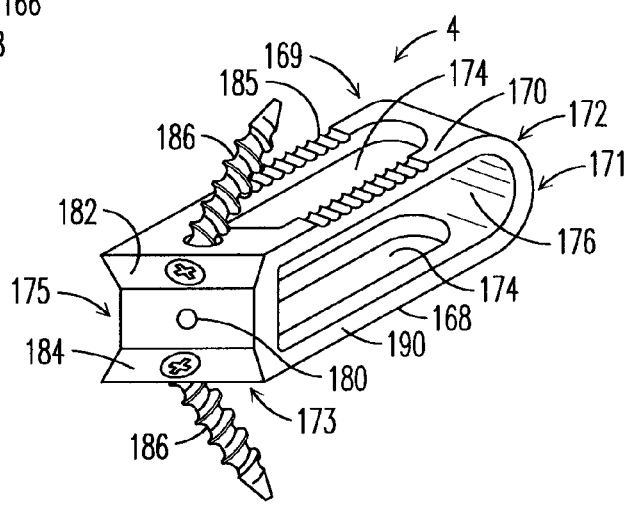
FIG. 8 is an isometric view of the spinal implant of FIG. 7 in an alternate orientation, according to the disclosure.

FIGS. 7 and 8 illustrate another embodiment of a spinal implant 4. The spinal implant 4 has an implant body 166 has an upper surface 168, a lower surface 170, a first side 188, and a second side 190. The implant body 166 also comprises a fusion portion 169 and an introduction portion 171. The fusion portion 9 may taper in a way similar to the taper of the fusion portion 11 of the implant spacer body 2 of FIGS. 1, 3 and 4 and the introduction portion 171 may taper in a way similar to the taper of the introduction portion 9 of the implant spacer body 2 of FIGS. 1, 3 and 4. The implant body 166 may have a plurality of passages or openings 174, 176 that may receive bone material when the spinal implant 4 is installed. The bone material of the spinal implant 4 fuses with bone material of adjacent vertebrae and better secures the spinal implant 4 to the vertebrae. The spinal implant 4 may have a tapered anterior end 172 that will facilitate installation into an inter-vertebral space. The spinal implant 4 also has a posterior end 173 comprising a chevron 175 or channel 175. The channel 175 has a first surface 182 and a second surface 184, through which bone screw passages are arranged that extend from the posterior end 173 to the upper surface and lower surface 168, 170. A delivery tool attachment location 180 is arranged proximate the posterior end 173. The bone screw passages may be countersunk so a bone head of the bone head screw 186 is at least flush with the first and second surfaces 182, 184 when installed. Bone screws 186 extend through the bone screw passage and into adjacent vertebrae. As illustrated, the bone screw passages have an opening that is centered on the first and second surfaces 182, 184. However, the bone screw passages may be arranged at any location on the first and second surfaces 182, 184 and the location may be determined by at least ease of bone screw 186 installation. The channel 175 may be sized to facilitate installation of the bone screws 186.

Figure 9A:
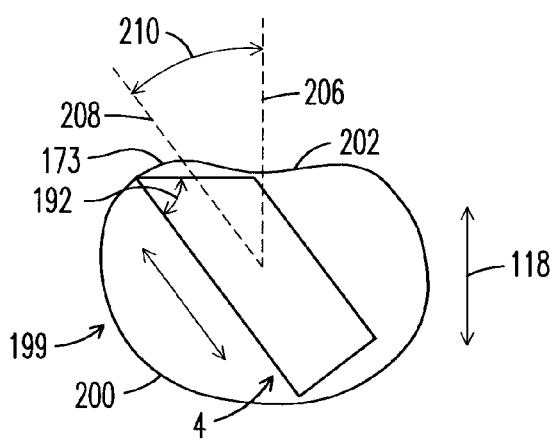
FIG. 9A is a top view of a spinal implant that is generally installed from a lateral posterior side of an inter-vertebral space according to another embodiment of the disclosure.
Figure 9B:
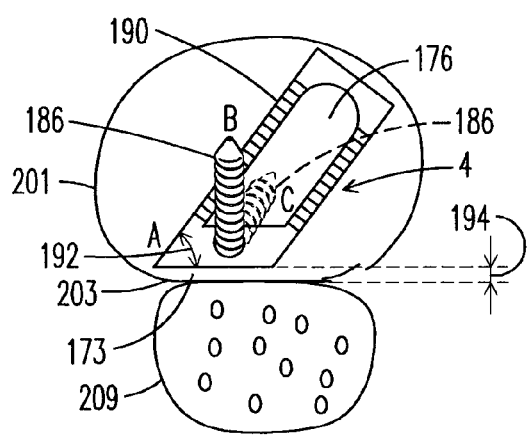
FIG. 9B is a bottom view of the spinal implant that is generally installed from a lateral posterior side of an inter-vertebral space according to another embodiment of the disclosure.

FIG. 9A top view of a spinal implant 4 that is generally installed from a lateral posterior side of an inter-vertebral space according to another embodiment of the disclosure and FIG. 9B is a bottom view of FIG. 9A. For convenience, the following discussion will be limited to the embodiment of the spinal implant 4 of FIGS. 7 and 8, but it is understood that the disclosure is not limited to the embodiment of spinal implant 4. Upper and lower vertebrae 201, 200 are illustrated and the spinal implant 4 is installed in an inter-vertebral space 199. A posterior surface 203 of the upper vertebrae 201 and a posterior surface 202 of the lower vertebrae 200 are also illustrated. As installed, the spinal implant 4 is skewed an amount 210 relative to the posterior to anterior axis 118. The skew amount 210 is an angular measure between an axis 206, which is parallel to the posterior to anterior axis 118, and an implant body centerline 208. The posterior end 173 of the spinal implant may be skewed a posterior-end-skew-amount 192, where the posterior-end-skew-amount 192 is an angular measure between the posterior end 173 and the first side 188, or the second side 190, when viewed from the top or bottom. The posterior end 173 of the spinal implant 4 may be skewed by the posterior-end-skew-amount 192 to facilitate positioning of the spinal implant 4. If the spinal implant 4 is installed in a skewed orientation as shown, a single spinal implant 4 may extend across the inter-vertebral space (in a lateral direction, which is perpendicular to a direction of the posterior to anterior axis 118). This may offer a more stable installation than a single spinal implant 4 installed in a direction parallel to the posterior to anterior axis 118. The spinal implant 4 is installed to be interior to the posterior surfaces 202, 203 of the lower and upper vertebrae 200, 201, respectively, by a distance 194. The spinal implant 4 may be a distance of about 4 mm from a nerve 209. Bone screws 186 extend into the upper and lower vertebrae 201, 200.

Figure 10A:
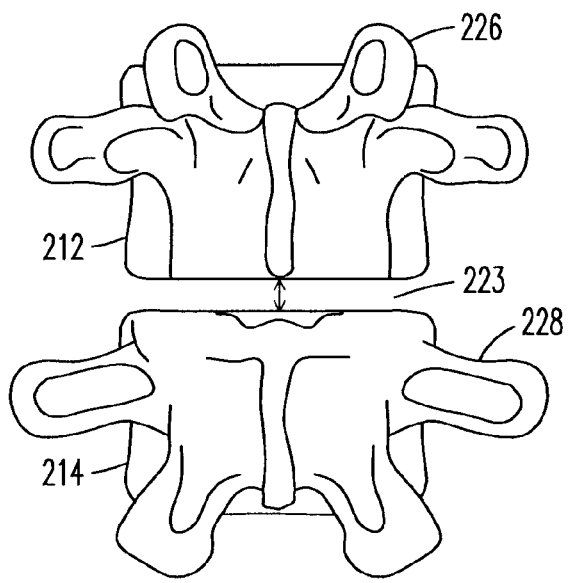
FIG. 10A is a posterior view of an inter-vertebral space between adjacent vertebrae having no implant installed.
Figure 10B:
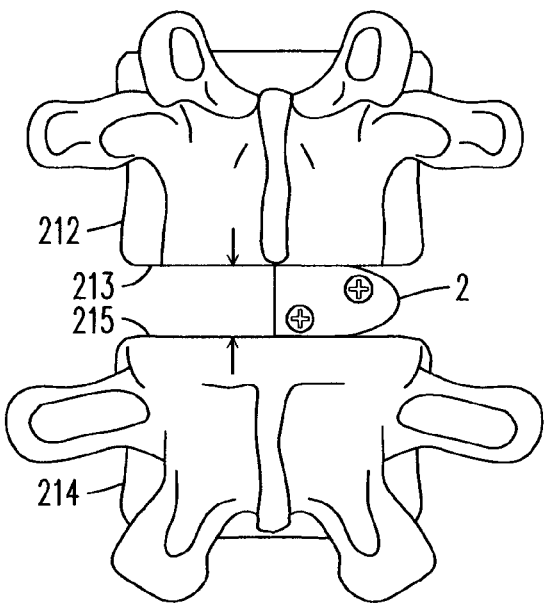
FIG. 10B is a posterior view of an inter-vertebral space between adjacent vertebrae having an implant as disclosed herein installed.
Figure 10C:
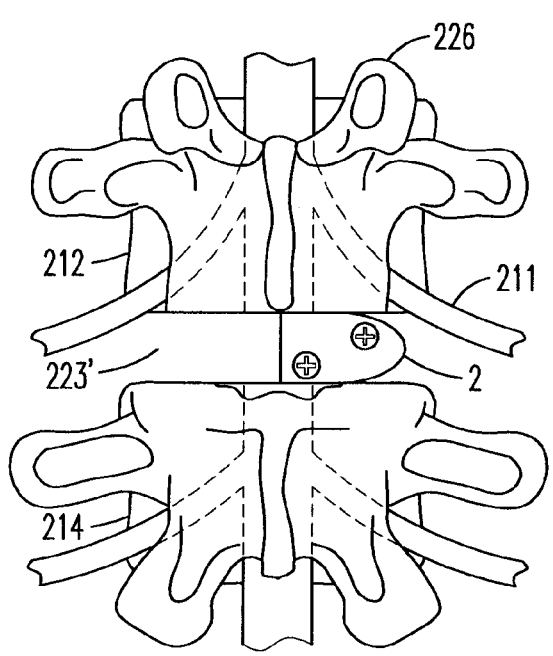
FIG. 10C is a posterior view of an inter-vertebral space between adjacent vertebrae having an implant as disclosed herein installed.
Figure 10D:
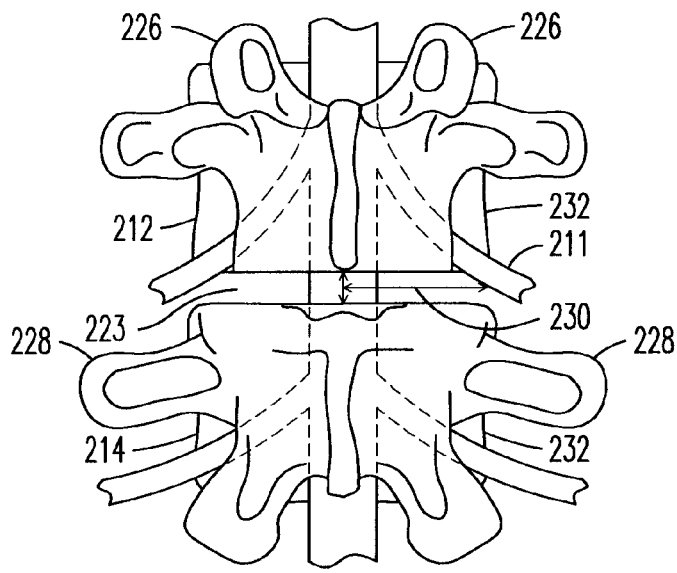
FIGS. 10D and 10E are posterior views of inter-vertebral spaces and the difference between a distance between adjacent vertebrae with and without an implant is illustrated.
Figure 10E:
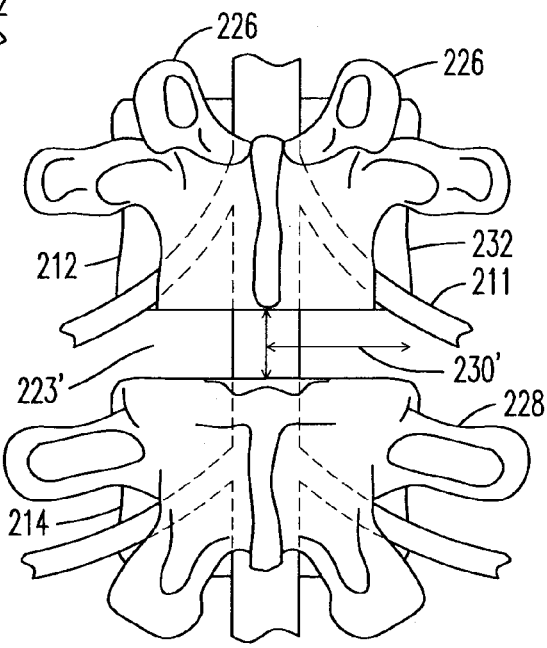
Figure 10F:
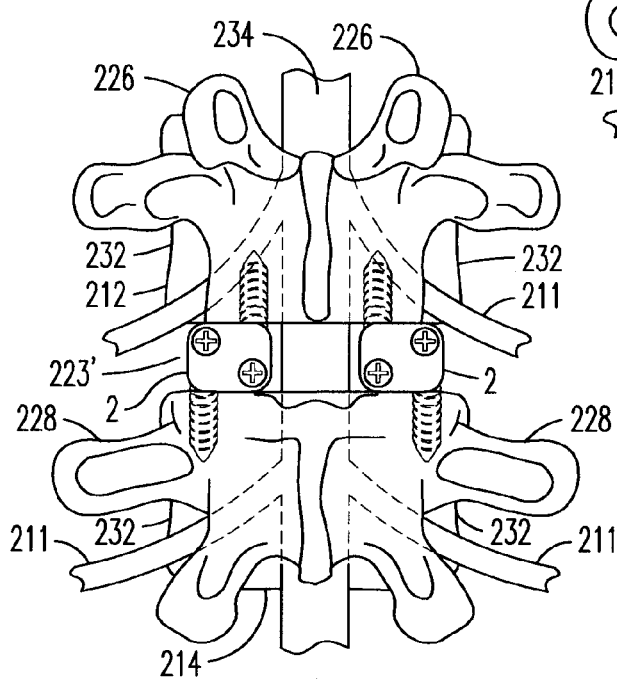
FIG. 10F is a posterior view of an inter-vertebral space between adjacent vertebrae having an implant as disclosed herein installed with a dural sac and nerves are illustrated.

FIGS. 10A and 10D show an inter-vertebral space 223 between adjacent vertebrae 212, 214 without a spinal implant installed and FIGS. 10B, 10C, 10E and 10F show an inter-vertebral space 223' between adjacent vertebrae 212, 214 with a spinal implant 2 installed. For convenience, the following discussion will be limited to the embodiment of the spinal implant 2 of FIG. 1, but it is understood that the disclosure is not limited to the embodiment of spinal implant 2. The inter-vertebral space 223 between adjacent vertebrae 212, 214 is smaller than the inter-vertebral space 223' between adjacent vertebrae 212, 214 when a spinal implant 2 is present in the inter-vertebral space 223'. It may be beneficial for the inter-vertebral space 223' to be greater because a distance 230' between a nerve 211 and a center of the inter-vertebral space increases and the nerve(s) 211 may be partly guided by pedicles 226, 228 in the upper and lower vertebrae 212, 214 respectively. For example, the distance 230 between the nerve 211 and the center of the inter-vertebral space 223 seen in FIG. 10D is not as great as the distance 230' between the nerve 211 and the center of the inter-vertebral space 223'. This increase in distance is due partly to the increase in inter-vertebral space that results from installation of the spinal implant 2. Furthermore, as illustrated in FIGS. 10D and 10E, the nerve is raised away from the inter-vertebral space 223' when the spinal implant 2 is installed. Illustrated more completely in FIG. 10F, nerves 211 are surrounded by a dural sac 234 and spinal implants 2 are installed in the inter-vertebral space 223'. A spacing between the nerves 211 and the inter-vertebral space 223' has been increased by the spinal implants 2 and the distance between the spinal implants 2 and the nerves 211 has been increased as well.

Figure 11A:
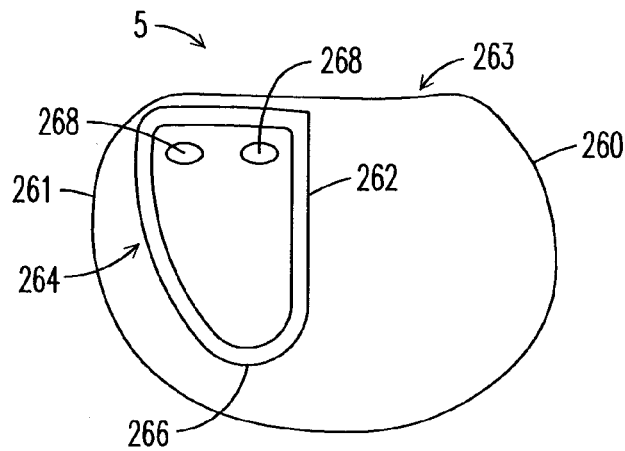
FIG. 11A is a top view of a spinal implant that is generally installed from a posterior side of an inter-vertebral space according to another embodiment of the disclosure.

FIG. 11A is a top view of a spinal implant 5 according to another embodiment of the disclosure. The spinal implant 5 comprises an implant body 262. Bone screw passages 268 are arranged toward a posterior end of the spinal implant 5 and the posterior end of the spinal implant 5 is interior to a posterior surface 263 of a vertebrae 260. A lateral surface 264 of the spinal implant 5 may be similar in shape or contour to a lateral surface 261 of the vertebrae 260.

Figure 11B:
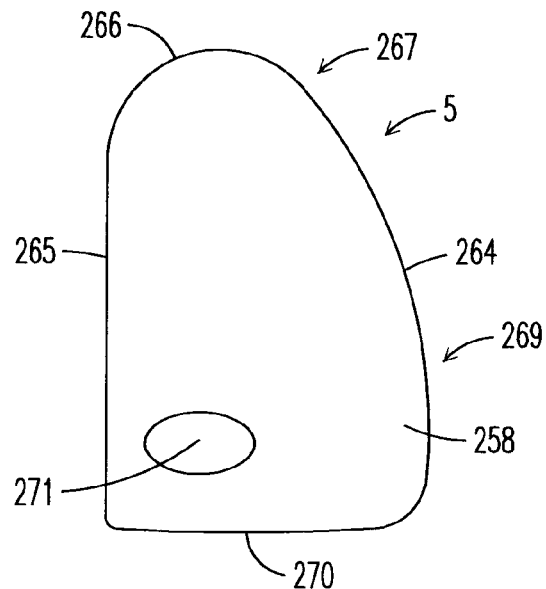
FIGS. 11B-11D are a top, front and right side view, respectively, of the spinal implant of FIG. 11A.
Figure 11C:
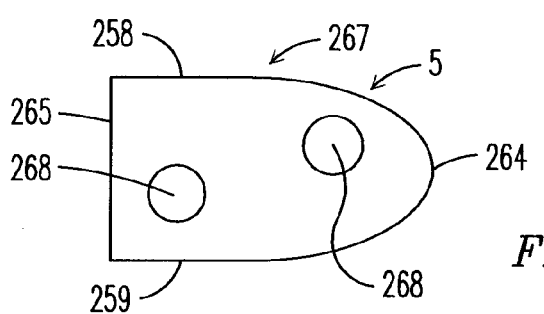
Figure 11D:
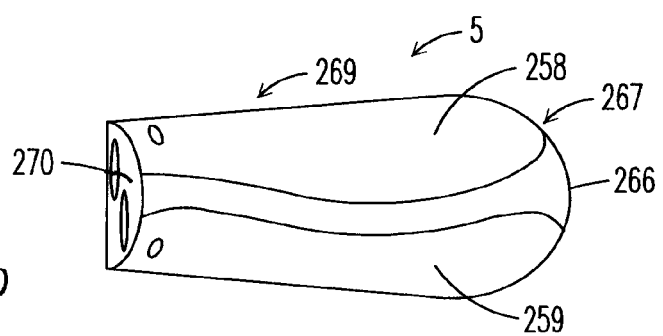

FIGS. 11B-11D are top, front and right side views, respectively, of the spinal implant 5 of FIG. 11A. The implant body 262 may be a tapered implant body 262, tapering from an upper surface 258 toward the lateral surface 264 and tapering from a lower surface 259 to the lateral surface 264. The implant body 262 may be thicker toward a first side 265. The upper surface 258 and the lower surface 259 of the implant body 262 may also taper generally from proximate the anterior surface 266 to a posterior surface 270. A bone-screw-passage-exit 271 may be elliptical or oval in shape to provide the bone screw with the latitude to move angularly (i.e. from side to side) to better align with the adjacent vertebrae and improve insertion of the bone screw into the vertebrae. An anterior end of the implant body 262 may have a tapering introduction portion 267, wherein the introduction portion 267 tapers toward the anterior surface 261 to at least facilitate installation of the spinal implant 5 in the inter-vertebral space. The implant body 262 may also comprise a fusion portion 269, which may taper to the posterior surface 270. The upper and lower surfaces 258, 259 may comprise a plurality of teeth or serrations (not shown) and the implant body 262 may comprise at least one channel that may be used for the introduction of bone material to at least promote fusion of the spinal implant 5 with the adjacent vertebrae.

The anterior surface 266 is illustrated as curved. The anterior surface 266 being curved offers the advantage of providing additional separation or distance from an adjacent nerve (see FIG. 10C). The first side 265 being thicker aids in raising a central portion between adjacent vertebrae, thereby increasing a distance between adjacent vertebrae. The increased distance may raise adjacent nerves associated with an upper vertebrae and lower adjacent nerves associated with a lower vertebrae to increase the distance between the nerves and the spinal implant 5. Furthermore, the anterior surface 266 curved as shown may also increase the distance between the spinal implant 5 and the adjacent nerves. The greater separation between the spinal implant 5 and the adjacent nerves is beneficial because it reduces the risk of the spinal implant 5 interfering with the adjacent nerves.

Figure 12A:
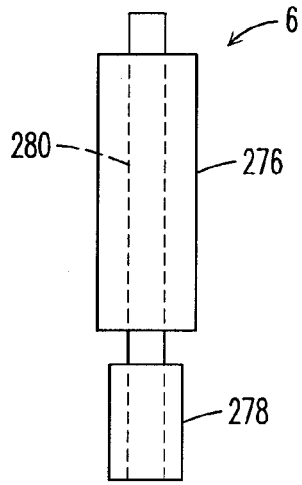
FIG. 12A is a top view of a spinal implant that is generally installed from a posterior side of an inter-vertebral space according to another embodiment of the disclosure.

FIG. 12A is a top view of a spinal implant 6 according to another embodiment of the disclosure. The spinal implant 6 is comprised of a first implant spacer body 276 and a second implant spacer body 278, with the first implant spacer body 276 and the second implant spacer body 278 being connected by a pin 280 or a rod 280. The first implant spacer body 276 and the second implant spacer body 278 are able to swivel or rotate relative to each other. The first implant spacer body 276 may be similar to other implant spacer bodies described herein and the plate may be similar to other plates describer herein. The second implant spacer body 278 may be rectangular in shape with a major axis 290 (see 12B) (i.e. the longer of the two axes) and a minor axis 291 (see 12B) (i.e. the shorter of the two axes). Alternate means of connecting the first implant spacer body 276 to the second implant spacer body 278 may be used as long as the first implant spacer body 276 and the second implant spacer body 278 are able to rotate or swivel relative to each other.

Figure 12B:
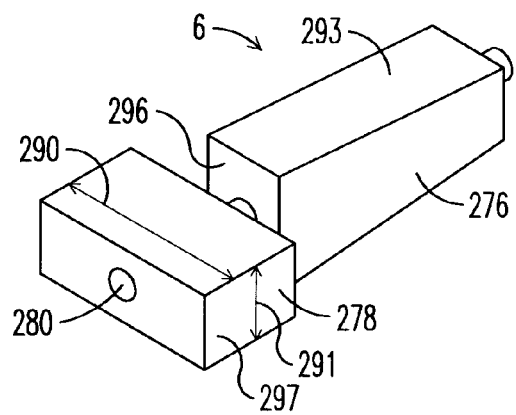
FIGS. 12B and 12C are isometric views of the spinal implant of 12A.
Figure 12C:
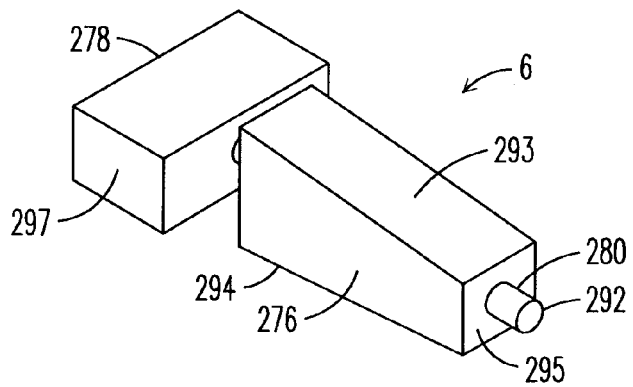
Figure 12D:
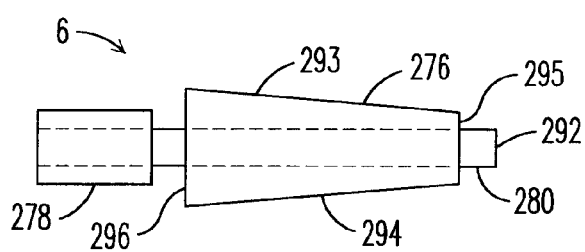
FIGS. 12D and 12E are side views of the spinal implant according to FIG. 12 illustrating the implant in an installation configuration and an operational configuration, respectively
Figure 12E:
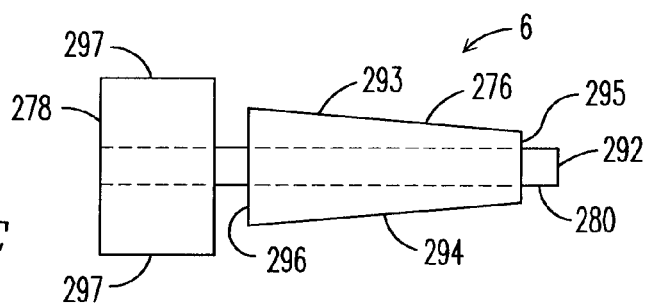

FIGS. 12B and 12C are isometric views of the spinal implant 6 and FIGS. 12D and 12E are side views of the spinal implant in an installation position and an operational position, respectively. The first implant spacer body 276 has an upper surface 293 and a lower surface 294, with the upper and lower surfaces 293, 294 tapering from a posterior surface 296 to an anterior surface 295. As with other embodiments disclosed herein, the first implant spacer body 276 may have an introduction portion and a fusion portion. The fusion portion may have a plurality of teeth or serrations. The second implant spacer body 278 is rigidly connected with the pin 280 such that when the pin 280 rotates, the second implant spacer body 278 rotates a same amount and in a same direction. The pin 280 has a pin end 292. The pin end 292 is operatively engages with an installation tool such that when a torque is applied to the installation tool, the pin and the second implant spacer body 278. The pin end 292 may have any interface as necessary to operatively engage with the installation tool. For example, the interface may be a Phillips head, a straight head, a hex head, a bolt head, or a key, to name but a few. The second implant spacer body 278 may have teeth or serrations arranged on end surfaces 297 of ends of the second implant spacer body 278 associated with the major axis 290.

Figure 13A:
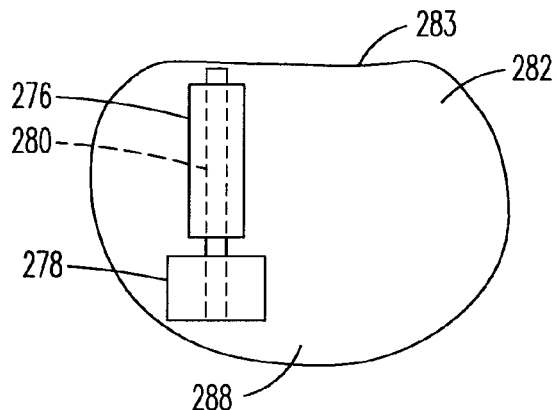
FIGS. 13A and 13B are top views of the spinal implant according to FIG. 12 illustrating the implant in an installation configuration and an operational configuration, respectively.
Figure 13B:
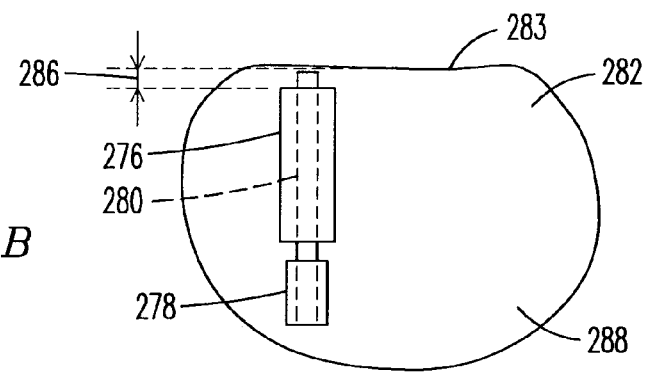
Figure 14A:
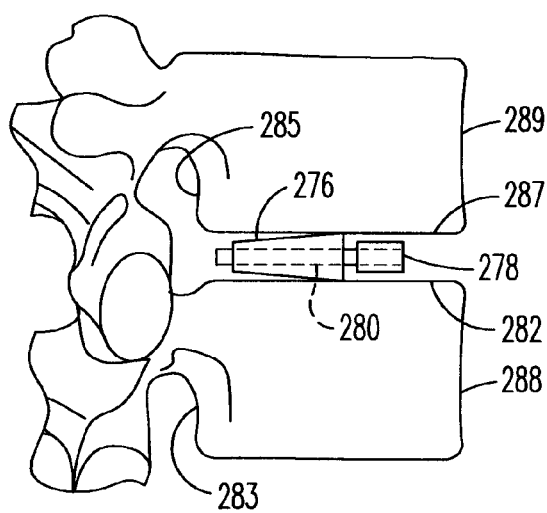
FIGS. 14A and 14B are side views of the spinal implant according to FIG. 12 illustrating the implant in an installation configuration and an operational configuration, respectively.
Figure 14B:
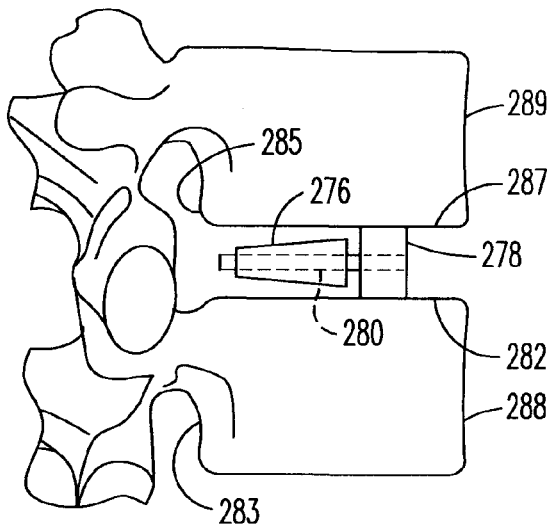

FIGS. 13A and 13B show top views of the spinal implant 6 of FIG. 12 in an installation position (13A) and an operational position (13B). FIGS. 14A and 14B show side views of the spinal implant 6 of FIG. 12 in an installation position (14A) and an operational position (14B). When installing the spinal implant 6, the spinal implant 6 is arranged with the major axis of the second implant spacer body 278 parallel to a bone plate 282, 287 of vertebrae 288, 289. The spinal implant 6 is installed in an inter-vertebral space such that a posterior end of the first implant spacer body 280 is a distance 286 from a posterior surface 283 of the vertebrae. The second implant spacer body 278 is then rotated an amount (approximately 90 degrees) to substantially align the minor axis to be parallel to the bone plate 282, 287. This may increase the vertical distance between adjacent vertebrae 288, 289, wherein the vertical distance is understood to mean the linear distance between adjacent vertebrae 288, 289.

Figure 15B:
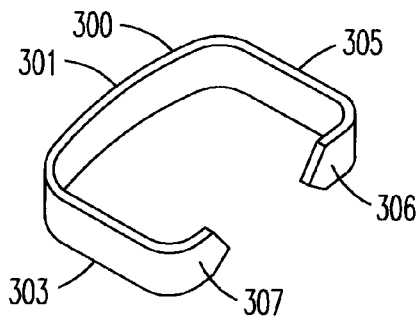
FIG. 15B is an isometric view of the locking device of FIG. 15A.
Figure 15A:
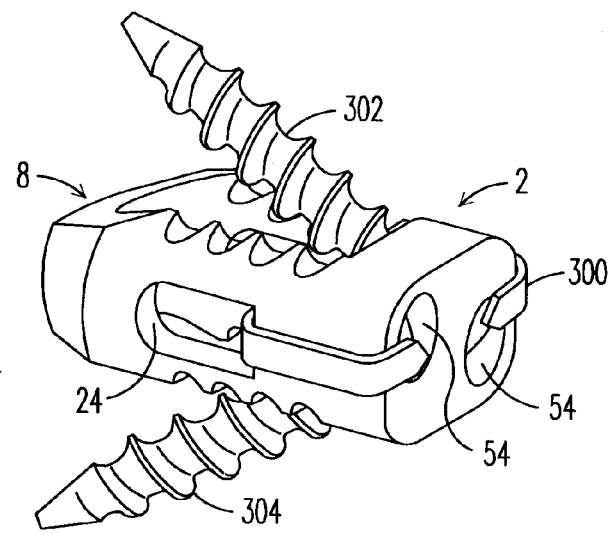
FIG. 15A is an isometric view of a spinal implant that is generally installed from a posterior side of an inter-vertebral space and locking device according to the disclosure.

FIGS. 15A-21B illustrate concepts of various locking devices or retaining devices that function to retain the bone screws in a secure position within the spinal implant. For convenience, the following discussion will be limited to the embodiment of the spinal implant 2 of FIG. 1, but it is understood that the locking devices disclosed herein are not limited to the embodiment of spinal implant 2 and may be used with any embodiment disclosed herein. FIGS. 15A and 15B are isometric views of a "band" type retaining device 300. The retaining device 300 is comprised of a first leg 301, a second leg 303 and a third leg 305 and is "U" shaped or channel shaped. Tabs 306, 307 are arranged and distal ends of the second and third legs 303, 305, relative to the first leg 301. The first leg 301, second leg 303 and third leg 305 should be sized so they are flexible enough to flex during installation of the retaining device 300 and rigid enough to retain bone screws 302 (a fixed angle screw), 304 (a semi-constrained poly-axial screw). In use, the retaining device is installed through openings 24 in the implant spacer body 8. When installed, the tabs 306, 307 will at least partly cover screw passages 54 and function to prevent the bone screws 302, 304 from exiting the implant spacer body 8. The retaining device 300 may be fabricated from any suitable material such as titanium or a biocompatible composite material.

Figure 16:
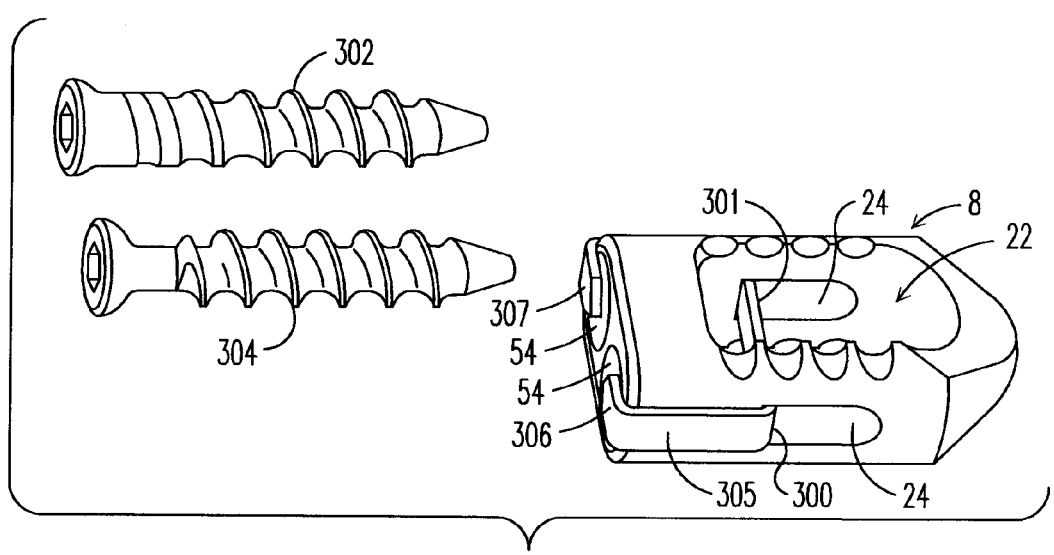
FIG. 16 is an isometric view of the locking device of FIG. 15A and FIG. 15B and bone screws.

FIG. 16 is an isometric view that shows the retaining device 300 installed in the implant spacer body 8 with bone screws 302, 304 removed. The first leg 301 of the retaining device 300 extends across the implant spacer body 8 from a first side to a second side. The retaining device is installed through openings 24 in the sides of the implant spacer body 8 with the first leg 301 being in the cavity 22 in the installed position.

Figure 17A:
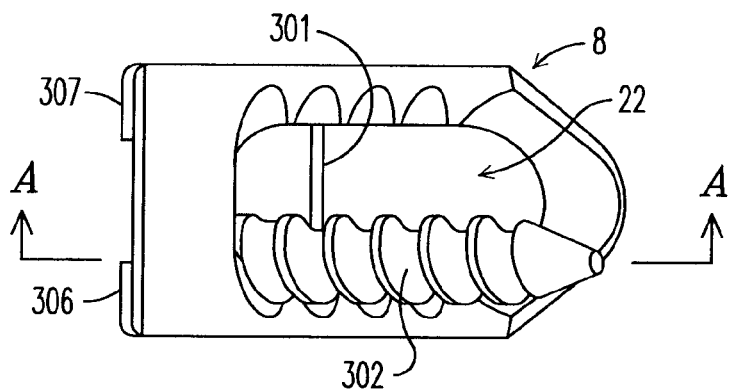
FIG. 17A is an isometric view of a spinal implant having the locking device of FIG. 15A and FIG. 15B and a fixed angle screw as illustrated in FIG. 16.
Figure 17B:
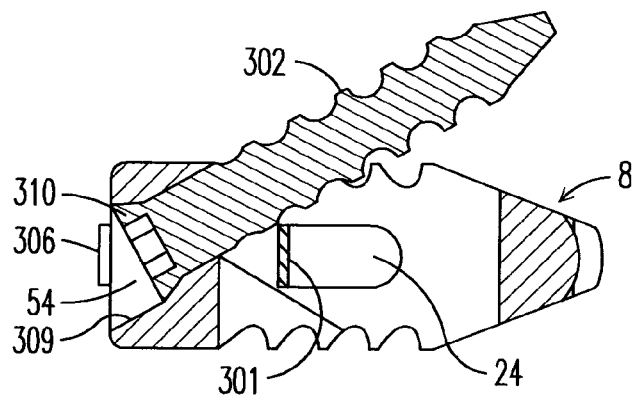
FIG. 17B is a view of section A-A of FIG. 17A.

FIG. 17A is a top view of an implant spacer body 8 having a fixed angle screw 302 installed in a bone screw passage 54. FIG. 17B is a view of Section A-A of FIG. 17A. The fixed angle screw 302 has a screw head 310 and installed in bone screw passage 54, which has a countersunk portion 309. A portion of tab 306 partially covers the bone screw passage 54 and will prevent the fixed angle screw 302 from exiting the implant spacer body 8.

Figure 18A:
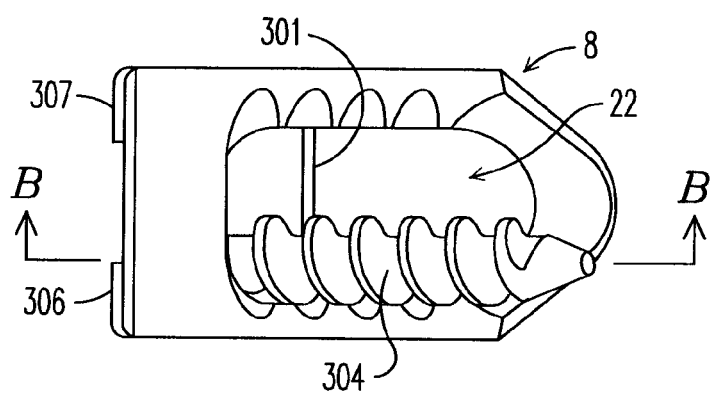
FIG. 18A is an isometric view of a spinal implant having the locking device of FIG. 15A and FIG. 15B and a semi-constrained poly-axial screw as illustrated in FIG. 16.
Figure 18B:
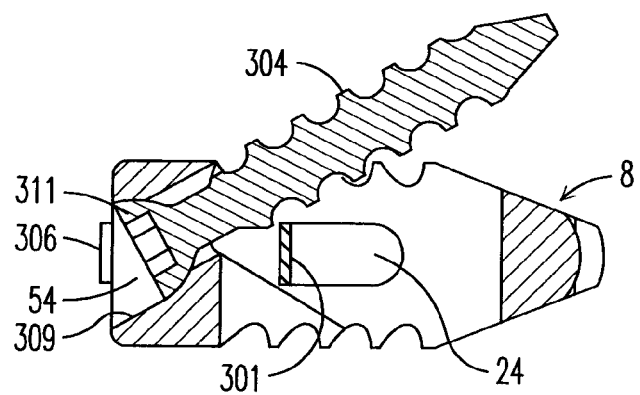
FIG. 18B is a view of section B-B of FIG. 18A.

FIG. 18A is a top view of an implant spacer body 8 having a semi-constrained poly-axial screw 304 installed in a bone screw passage 54. FIG. 18B is a view of Section B-B of FIG. 18A. The fixed angle screw 304 has a screw head 311 and installed in bone screw passage 54, which has a countersunk portion 309. A portion of tab 306 partially covers the bone screw passage 54 and will prevent the semi-constrained poly-axial screw 304 from exiting the implant spacer body 8.

Figure 19:
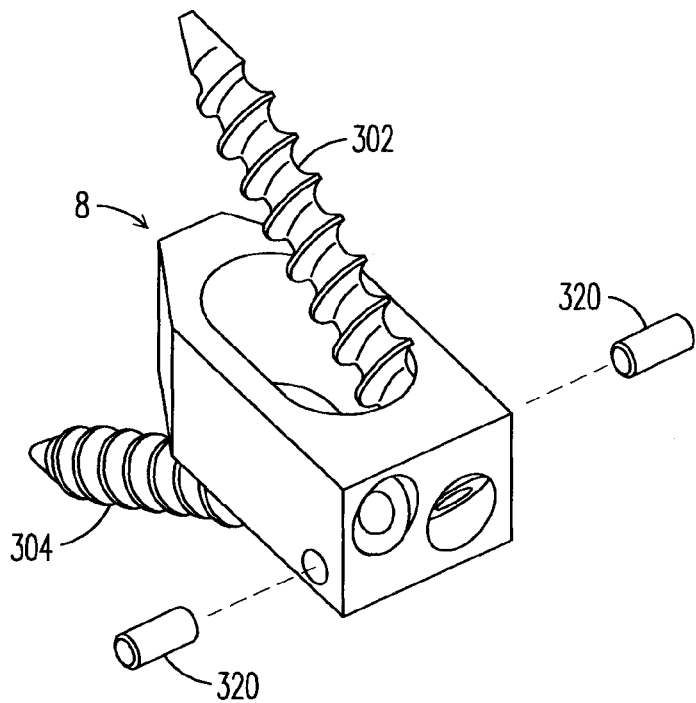
FIG. 19 is an isometric view of a locking device having pins.

FIG. 19 shows another locking device according to another embodiment of the disclosure. Pins 320 are installed in the implant spacer body 8 and retain bone screws 302, 304 by contacting the bone screws 302, 304 and prevent them from rotating.

Figure 20:
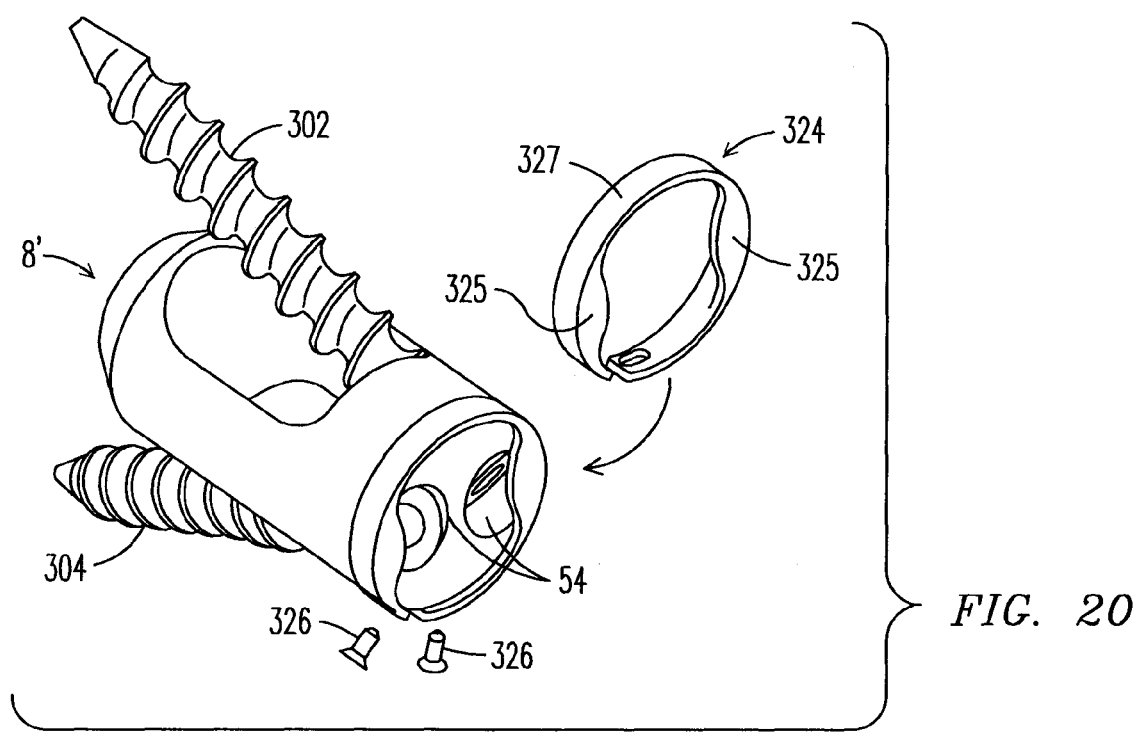
FIG. 20 is an isometric view of a split ring type locking device.

FIG. 20 shows another locking device according to another embodiment of the disclosure. A split ring 324 having a body 327 is installed on the posterior end of the implant spacer body 8'. The split ring 324 has additional material 325 added to the interior circumference of the body 327. The additional material 325 partly covers the bone screw passages 54 to prevent the bone screws 302, 304 from exiting the implant spacer body 8'. Pins 326 are installed through holes in the split ring 324 and extend into the implant spacer body 8 and secure the split ring 324 to the implant spacer body 8.

FIGS. 21A and 21B illustrate another locking device according to another embodiment of the disclosure. A plate 340 is secured to a posterior surface 341 of an implant spacer body 8". The plate is secured to the implant spacer body by pins 342 or screws 342. The plate 340 covers the bone screw passages 54 and prevents the bone screws 302, 304 from exiting the implant spacer body 8".

FIG. 22 shows a tool 349 used to install a bone screw 186 into a vertebrae to secure a spinal implant 4 in an inter-vertebral space. The tool 349 is discussed in the context of use with the spinal implant disclosed in FIGS. 7 and 8. However, the tool 349 may be used to install a bone screw 186 being used with any embodiment discussed herein. The tool 349 comprises a rigid portion 350 and a flexible portion 352. The flexible portion 352 may articulate and vary in orientation as necessary. An angle of the channel surfaces 182, 184 may influence the amount of articulation required by the flexible portion 352 to install the bone screw 186. A temporary septum 360 is attached to the implant spacer body 166 at a delivery tool attachment location 180, and urges the flexible portion 352 toward a bone screw head 356 so a tip 354 of the flexible portion 352 may engage with the screw head 356 and apply a torque to the bone screw 186. Once the bone screws 186 are installed, the septum 360 is removed.

It is generally contemplated that all of the spinal implant embodiments of the present disclosure can be made from any bio-compatible or physically inert material or combination of such materials having the mechanical strength capable of maintaining the intervetebral space between adjacent vertebrae without impinging upon nerves and/or restricting movement and further bone growth or regeneration of the spinal column discs adjacent the intervetebral space in which the present invention is mounted. Examples of such materials can include bone, such as bone sections from a femur or other bones of the patient or from donors, metal materials such as titanium, titanium alloys, stainless steel, chrome, cobalt, and other, similar materials, as well as various polymeric materials such as methyl methacrylate (MMA), urethane, polyacetal material, reinforced polymers such as carbon fiber or polyether keytone, polycarbonates, polypropylene, polyamides, and silicone based polymers as generally understood in the art.

Generally, to install the spinal implant, an incision is made in the patient's back in the region of the spine in need of repair (i.e. in the posterior of the patient). Once the incision is made, the damaged disk material between adjacent vertebrae is removed. A spinal implant will then be installed in the now vacant inter-vertebral space between adjacent vertebrae using appropriate installation tools. The spinal implant is then installed in the patients spine between the adjacent vertebrae using appropriate installation tools. The spinal implant is preferably installed from the posterior into the inter-vertebral space. Once the spinal implant is installed, the spinal implant can be anchored to the vertebrae with an appropriate number of bone screws. Thereafter, the installation tools or instruments can be removed and the surgical opening in the patient's back closed.

The spinal implant of FIG. 6 may be installed in a similar manner as disclosed. However, the first end of the spinal implant is positioned on one side of the spinal cord and rotated into position such that the first end of the spinal implant and the second end of the spinal implant will be at the posterior of the inter-vertebral space. The implant can be anchored to the vertebrae with an appropriate number of bone screws through bone screw passages in the plates. Thereafter, the installation tools or instruments can be removed and the surgical opening in the patient's back closed.

The present disclosure thus provides a simple device, typically made from a single, biocompatible material with minimal parts and generally utilizing only a minimal presences of screws, or similar fasteners to attach the flexible plate implant to the adjacent vertebrae of the patient and eliminates the need for a rod and screw system typically installed in pedicles of adjacent vertebrae.

It will be understood by those skilled in the art that while the foregoing has been described with reference to preferred embodiments and features, various modifications, variations, changes and additions can be made thereto without departing from the spirit and scope of the disclosure. For example, the figures and disclosure contained herein are directed to a spinal implant for use in a lumbar region of a spinal column. However, the concepts as disclosed may be directed to a spinal implant for application in another region of the spine, such as the thoracic region of the spine.

I claim:

1. An implant, comprising:
   an implant spacer body defining an upper surface, a lower surface, a posterior surface, and an anterior surface, at least one of said upper surface or said lower surface at least partially tapering from said anterior surface to said posterior surface at a predetermined first angle with respect to an implant spacer body centerline;
   a plate mechanically connected to said implant spacer body, said plate having a plate posterior surface and a plate anterior surface, said plate anterior surface arranged adjacent said body posterior surface, wherein said plate further defines at least two screw passages extending through said plate from said plate posterior surface to said plate anterior surface, each screw passage oriented at a predetermined second angle with respect to said implant spacer body centerline; and
   a screw to be received by each of said screw passages, each of said screws extending through said plate, from said plate posterior to said plate anterior.

2. The implant of claim 1, wherein said upper surface of said implant spacer body tapers from said anterior surface to said posterior surface at said predetermined first angle with respect to said implant spacer body centerline.

3. The implant of claim 2, wherein said lower surface of said implant spacer body tapers from said anterior surface to said posterior surface at a predetermined third angle with respect to said implant spacer body centerline.

4. The implant of claim 3, wherein said predetermined first angle and said predetermined third angle are approximately equal.

5. The implant of claim 4, wherein the first predetermined angle has a measure in the range of 2 degrees to 15 degrees.

6. The implant of claim 1, wherein said plate is mechanically connected to said implant spacer body by a mechanical connector selected from the group consisting of a screw, a rivet, a mechanical clip, a welded joint, a pin, and/or combinations thereof.

7. The implant of claim 1, wherein said upper surface and said lower surface are serrated surfaces.

8. The implant of claim 1, wherein said plate comprises 4 screw passages.

9. An inter-vertebral installation, comprising:
   a three-dimensional, wedge-shaped spacer component arranged within an inter-vertebral space between two adjacent vertebrae, said spacer component extending from a posterior of said inter-vertebral space toward an anterior of said inter-vertebral space, wherein said spacer component has an upper surface arranged proximate an upper vertebrae end plate and a lower surface arranged proximate a lower vertebrae end plate, said upper surface and said lower surface of said spacer component tapering to a spacer component thin edge, from said anterior to said posterior;
a plate component having a plate component anterior surface attached to said spacer component thin edge, said plate component defining at least two screw passages that diverge, wherein a first screw passage extends through said plate component toward said upper surface and a second screw passage extends through said plate toward said lower surface; and
a screw received by each screw passage, wherein each of said screws extends from said posterior toward said anterior and into either said upper vertebral end plate or said lower vertebral end plate, and wherein said spacer component, a screw head of each of said screws, and said plate component reside fully within said inter-vertebral space.

10. The inter-vertebral installation of claim 9, wherein said plate component further comprises a plate component posterior surface, said plate component posterior surface being opposite said plate component anterior surface; and wherein said plate component posterior surface is at least a depth of 3 millimeters from a vertebrae posterior surface.

11. The inter-vertebral installation of claim 9, wherein said plate component further comprises a plate component posterior surface, said plate component posterior surface being opposite said plate component anterior surface; and wherein said plate component posterior surface is at least a depth of 5 millimeters from a vertebrae posterior surface.

12. The inter-vertebral installation of claim 9, wherein a first inter-vertebral spacer is arranged toward a lateral left side of said inter-vertebral space and a second inter-vertebral spacer is arranged toward a lateral right side of said inter-vertebral space.

13. The inter-vertebral installation of claim 9, wherein said upper surface and said lower surface of said spacer component are serrated.

14. The inter-vertebral installation of claim 9, wherein said spacer component, and said plate component, and said screws are fabricated from a biocompatible material.

15. An inter-vertebral installation comprising:
a spacer component having an upper surface and a lower surface such that the upper surface and the lower surface taper from an anterior to a posterior, wherein the upper surface contacts a first bone plate of a first vertebrae and the lower surface contacts a second bone plate of a second vertebrae;
a plate component arranged proximate a posterior end of the spacer, wherein the plate component has a plate upper surface and a plate lower surface;
a pin connecting the spacer component with the plate component such that the spacer component and the plate component can rotate relative to each other; and
at least one bone screw passage arranged in the plate and oriented to direct a bone screw into either the first vertebrae or the second vertebrae.

16. An inter-vertebral implant installation comprising:
a spacer component having at least a fusion segment with an upper surface and a lower surface such that the upper surface and the lower surface taper from an anterior to a posterior, wherein the upper surface contacts a first bone plate of a first vertebrae and the lower surface contacts a second bone plate of a second vertebrae;
at least one bone screw passage arranged at the posterior of the spacer and oriented to accept a bone screw oriented with the screw head to the posterior and the screw threaded segment toward the anterior; and
a bone screw extending through the screw passage from the posterior and into the first bone plate, attaching the spacer component to the vertebrae.

17. An inter-vertebral implant comprising;
a spacer body defining an upper surface, a lower surface, a posterior end, an anterior end, a body-introduction portion at the anterior end, and a fusion portion to the posterior of said body-introduction portion, said fusion portion being of length greater than the length of the body-introduction portion and said fusion portion tapering from its anterior to its narrower posterior; and
a mounting element at the posterior end of said spacer body, said mounting element including at least two screw passages, each passage oriented to accept a bone screw oriented with the screwhead to the posterior of the implant and the screw threaded segment toward the anterior of and adjacent to the spacer body.

* * * * *